(12) United States Patent
Tokunaga

(10) Patent No.: US 8,513,021 B2
(45) Date of Patent: Aug. 20, 2013

(54) CONTROL METHOD OF MEASURING APPARATUS AND MEASURING APPARATUS

(75) Inventor: Kazutoshi Tokunaga, Kakogawa (JP)

(73) Assignee: Sysmex Corporation, Kobe (JP)

( * ) Notice: Subject to any disclaimer, the term of this patent is extended or adjusted under 35 U.S.C. 154(b) by 1437 days.

(21) Appl. No.: 11/361,169

(22) Filed: Feb. 24, 2006

(65) Prior Publication Data

US 2006/0195283 A1    Aug. 31, 2006

(30) Foreign Application Priority Data

Feb. 25, 2005    (JP) .................................. 2005-050514

(51) Int. Cl.

| G01N 35/08 | (2006.01) |
|---|---|
| G01N 21/00 | (2006.01) |
| G01N 31/00 | (2006.01) |
| G01N 33/00 | (2006.01) |
| G05B 19/18 | (2006.01) |
| G05B 21/00 | (2006.01) |
| G06F 7/38 | (2006.01) |
| G06F 9/00 | (2006.01) |
| G06F 9/44 | (2006.01) |

(52) U.S. Cl.
USPC ...... 436/55; 422/62; 422/67; 700/3; 700/266; 712/227

(58) Field of Classification Search
USPC ................ 422/67, 99, 62, 68.1, 105; 436/43, 436/50, 55; 702/22, 25, 30–32, 19, 108, 702/127; 700/1–5, 23, 266, 275, 281–285, 700/11–13, 253; 712/31, 32
See application file for complete search history.

(56) References Cited

U.S. PATENT DOCUMENTS

| 4,483,927 A | 11/1984 | Takekawa |
| 4,803,613 A * | 2/1989 | Kametani et al. ................. 700/3 |
| 5,397,539 A | 3/1995 | Hayashi et al. |
| 5,428,470 A * | 6/1995 | Labriola, II .................... 398/109 |
| 5,740,185 A * | 4/1998 | Bosse ............................ 714/749 |
| 6,192,945 B1 | 2/2001 | Ford et al. |
| 6,391,623 B1 | 5/2002 | Besemer et al. |
| 2003/0032191 A1 | 2/2003 | Hilson et al. |
| 2009/0113183 A1* | 4/2009 | Barford et al. ................ 712/220 |

FOREIGN PATENT DOCUMENTS

| JP | 62-173896 A | 7/1987 |
| JP | 11-237384 A | 8/1999 |
| WO | WO 2004/059288 A2 | 7/2004 |

OTHER PUBLICATIONS

European Search, Report for Application No. EP06003813 dated Nov. 15, 2006.

* cited by examiner

Primary Examiner — Jill Warden
Assistant Examiner — Charles D Hammond
(74) Attorney, Agent, or Firm — Brinks Hofer Gilson & Lione

(57) ABSTRACT

A measuring apparatus has a master communication interface for sequentially transmitting an operation command issued by a CPU to a plurality of mechanism units used for measurement of an analyte. The measuring apparatus also has a slave communication interface, provided for each mechanism unit, for receiving the operation command and a plurality of driving circuits for deriving the mechanism units in accordance with the received operation command. The master communication interface broadcasts an operation start instructing signal to the plurality of mechanism units after sequentially transmitting operation commands respectively to the plurality of mechanism units, and triggered by the operation start instructing signal, the driving units of the plurality of mechanism units concurrently initiate execution of the operation commands.

24 Claims, 13 Drawing Sheets

CONTROL METHOD OF MEASURING APPARATUS AND MEASURING APPARATUS

This application claims priority under 35 U.S.C. §119 to Japanese Patent Application No. 2005-050514 filed Feb. 25, 2005, the entire content of which is hereby incorporated herein by reference.

FIELD OF THE INVENTION

The present invention relates to a control method for operating a measuring apparatus, and to a measuring apparatus used for implementing the control method.

BACKGROUND

Measuring apparatuses such as a blood analyzer, a urine analyzer, a stool analyzer, a particulate analyzer and the like are known which are used for measuring various properties of a blood analyte, a urine analyte, a stool analyte, a particulate analyte and the like. As for such a measuring apparatus, there is disclosed an automatic analyzing apparatus which comprises a cartridge having a specimen tub for holding a specimen and a plurality of integrally formed reaction tubs, a conveyance mechanism part for conveying the cartridge, a plurality of dispersing units having multiple structures, and a photometric unit having multiple structures, wherein individual analytical processes are executed in parallel (see U.S. Pat. No. 5,397,539). In the automatic analyzing apparatus disclosed in U.S. Pat. No. 5,397,539, a specimen put in the specimen tab of the cartridge is first dispensed into the reaction tubs of the cartridge, and test reagents appropriate for individual analyses carried out in each reaction tubs are simultaneously dispensed at a plurality of predetermined positions during the course of conveyance of the cartridge. Then, the photometric unit having multiple structures concurrently conducts a photometry for the reaction solutions having completed the reaction in the respective reaction tubs. Therefore, a measuring apparatus of the above type has various mechanism units such as an analyte aspiration unit that aspirates an analyte from an analyte container containing the analyte, a reagent aspiration unit that aspirates a reagent from a reagent container containing the reagent, and a fluid unit that allows passage of the aspirated analyte and reagent, and all of which are designed to operate synchronously.

Such a conventional measuring apparatus has a structure as illustrated below. FIG. 13 is a block diagram showing the structure of a conventional measuring apparatus. As shown in FIG. 13, the conventional measuring apparatus 111 has a controller 112 and a plurality of mechanism units 113-115. The controller 112 is provided with a CPU 112a, a micro interface 112b and a plurality of driving circuits 112c, 112d. The driving circuit 112c is a circuit for driving motors, and the driving circuit 112d is a circuit for driving magnetic valves. The mechanism unit 113 is an arm unit having a pipette for aspirating an analyte, and the mechanism unit 113 is provided with a plurality of stepping motors 113a, 113b. The mechanism unit 114 is a fluid unit for allowing passage of a cleaning solution, and provided with a plurality of magnetic valves 114a, 114b and a plurality of stepping motors 114c, 114d. The mechanism unit 115 is an arm unit having a pipette for aspirating a reagent, and the mechanism unit 115 is provided with a plurality of stepping motors 115a, 115b.

The CPU 112a of the controller 112 is connected to the driving circuits 112c, 112d via the micro interface 112b, and is able to transmit a control signal from the CPU 112a to each of the driving circuits 112c, 112d. The driving circuit 112c is connected with the stepping motors 113a, 113b, 114c, 114d, 115a, 115b, and this driving circuit 112c is able to independently drive the stepping motors 113a, 113b, 114c, 114d, 115a, 115b concurrently. The driving circuit 112d is connected to the magnetic valves 114a, 114b, and the magnetic valves 114a, 114b may be independently and concurrently driven by the driving circuit 112d. A control signal transmitted from the CPU 112a is received by the driving circuits 112c, 112d, and in accordance with this control signal, the driving circuits 112c, 112d concurrently drive the stepping motors 113a, 113b, 114c, 114d, 115a, 115b and the magnetic valves 114a, 114b. As a result, these stepping motors 113a, 113b, 114c, 114d, 115a, 115b and magnetic valves 114a, 114b operate synchronously.

In the conventional measuring apparatus described above, however, since the driving circuits of the controller are directly connected to devices such as motors and magnetic valves provided for the mechanism units mounted in the measuring apparatus, it is necessary to configure the entire controller, including the driving circuits, in accordance specifically with the type and number of the devices accompanying the mechanism units. For this reason, in order to modify an already-set-up measuring apparatus such that the modified measuring apparatus will have an additional measurement item, or the modified measuring apparatus will have a different throughput, for example, it is necessary to add a mechanism unit or to change a part of the mechanism units, and hence it is necessary to modify the design of the controller in accordance with such a modification. Thus, in the current state of the art, the basis for efficiently developing various types (models) of measuring apparatuses is not sufficient, and there is still a problem that the product cost of the measuring apparatus is high.

SUMMARY

The scope of the present invention is defined solely by the appended claims, and is not affected to any degree by the statements within this summary.

The first aspect of the present invention relates to a control method of an operation of a measuring apparatus having a plurality of mechanism units used for measurement of an analyte, the method comprising steps of: issuing operation commands corresponding to each mechanism units by an operation instructor that instructs the operation of a plurality of mechanism units; sequentially transmitting by a first communicator provided in correspondence with the operation instructor, the operation commands issued by the operation instructor to the corresponding mechanism units; respectively receiving by a plurality of second communicators provided in correspondence with each of the mechanism units, the operation commands transmitted from the first communicator; temporarily storing by a plurality of drivers provided in correspondence with the respective mechanism units, the corresponding operation commands received by the second communicators; concurrently transmitting by the first communicator, an operation start instructing signal for instructing the start of operation to the plurality of mechanism units; received by the second communicators, the operation start instructing signal transmitted from the first communicator; and respectively driven by the drivers, the corresponding mechanism units in accordance with the corresponding stored operation commands upon reception of the operation start instructing signal by the second communicators.

The second aspect of the present invention relates to a measuring apparatus conducting measurement of an analyte, the apparatus comprising: a plurality of mechanism units; an operation instructor that issues operation commands corresponding to each of the plurality of mechanism units; a first communicator, provided in correspondence with the operation instructor, for sequentially transmitting the operation commands issued by the operation instructor to the corresponding mechanism units; a plurality of a second communicator, provided in correspondence with each mechanism unit, for receiving the operation command transmitted from the first communicator; and a plurality of drivers, provided in correspondence with each of the mechanism units, for driving the mechanism units in accordance with the operation commands received by the corresponding second communicators, wherein the first communicator concurrently transmits an operation start instructing signal for instructing starting of operation to the plurality of mechanism units, after sequentially transmitting the operation commands to the plurality of mechanism units; and the driver drives the corresponding mechanism unit in accordance with the operation command given from the corresponding second communicator, when the second communicator receives the operation start instructing signal.

The third aspect of the present invention relates to a measuring apparatus conducting measurement of an analyte, the apparatus comprising: a plurality of mechanism units having a detector; a controller that controls operation of the plurality of mechanism units; a detection result memory, provided in correspondence with the mechanism unit, for storing a detection result; a command issuer that issues a state acquisition command for acquiring the state of the mechanism unit detected by each detector; a first communicator that concurrently transmits the state acquisition command issued by the command issuer to the plurality of mechanism units; and a plurality of second communicators provided in correspondence with mechanism units, for receiving the state acquisition command transmitted from the first communicator, wherein the second communicator transmits the detection result stored in the detection result memory to the controller.

DETAILED DESCRIPTION OF THE PREFERRED EMBODIMENT

In the following, an embodiment of the present invention will be explained on the basis of the attached drawings.

Figure 1:
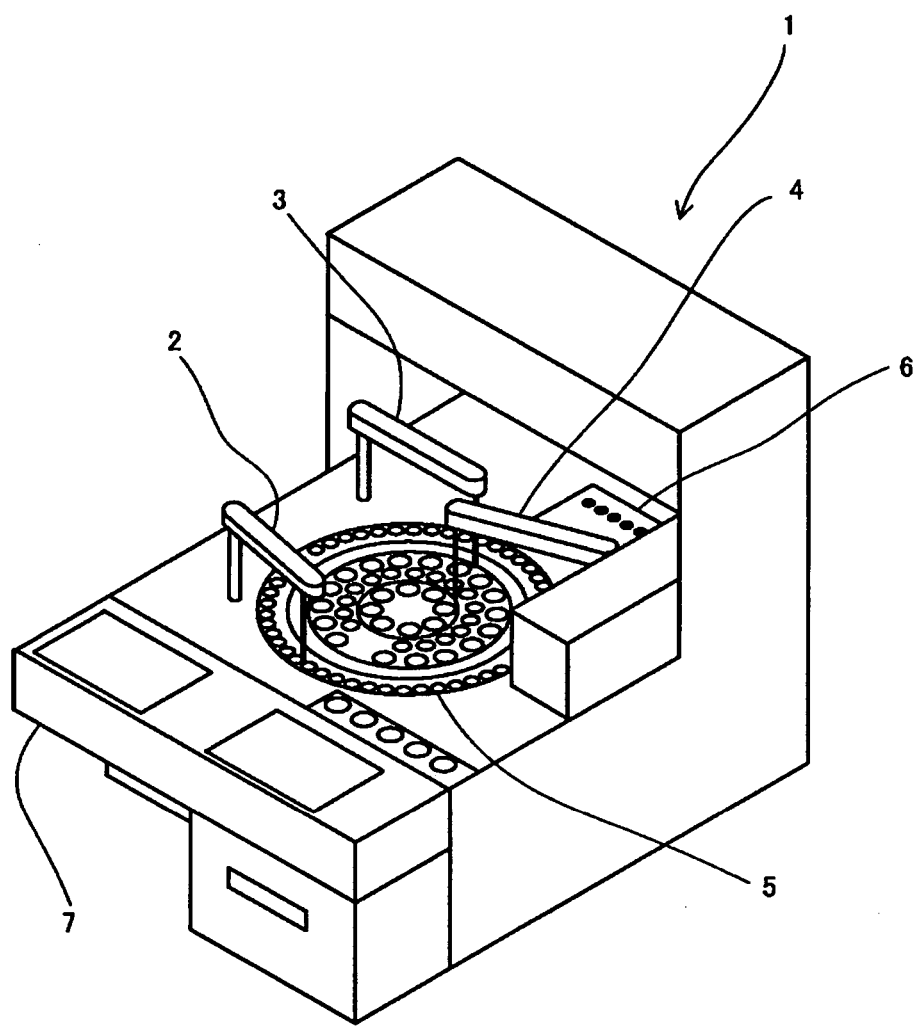
FIG. 1 is a perspective view showing an overview of a measuring apparatus of an embodiment.

FIG. 1 is a perspective view showing an overview of a measuring apparatus of the present embodiment. A measuring apparatus 1 according to the present embodiment is a blood coagulation measuring apparatus dedicated for testing coagulation of a blood analyte. As shown in FIG. 1, the measuring apparatus 1 according to the present embodiment has an analyte dispensing arm unit 2 used for dispensing of a blood analyte, reagent dispensing arm units 3, 4 used for dispensing of reagents, a table unit 5 for holding a cuvette and a reagent container, an optical detection unit 6 for detecting a degree of coagulation of measured sample, and a conveyance unit 7 for conveying a blood analyte. In the measuring apparatus 1, a user or an external automatic conveyer manually/automatically places a rack (not shown) holding a plurality of analyte containers containing blood analytes, on the conveyance unit 7, to the provide blood analytes. When the rack is placed on the conveyance unit 7, the placed rack is conveyed to a predetermined analyte aspirating position by the conveyance unit 7. When the rack is conveyed to the analyte aspirating position by the conveyance unit 7, the analyte dispensing arm unit 2 aspirates a specific amount of blood analyte from the blood container held by the rack, and discharges the blood analyte into a cuvette detachably mounted on the table unit 5. To the table unit 5, a plurality of reagent containers containing reagents are detachably mounted, and a specific amount of reagent is aspirated from a reagent container with one or both of the reagent dispensing arm units 3, 4, and the reagent is discharged to the cuvette containing the blood analyte. In this manner, a test sample in which a blood analyte and a reagent are mixed is prepared. A cuvette containing such a test sample is transferred to the detection unit 6 from table unit 5 by a transferring unit (not shown). In the detection unit 6, the cuvette is heated to a predetermined temperature for a predetermined time, and then a degree of coagulation of the test sample is optically detected. The detection unit 6 may measure a time for blood coagulation based on a biological activation method, or may measure a variation in absorbance when a specific reagent and a chromogenic synthetic substrate are added to blood based on a synthetic substrate method, or may measure a variation in absorbance when a stabilizing reagent and an antibody sensitization reagent are added to blood or serum base on a turbidimetric immunoassay. The measuring apparatus 1 is connected to a data processor (not shown) implemented by a computer via a LAN, a LAN cable, a serial communication wire or the like communication medium so as to allow data communication. The data detection results obtained by the detection unit 6 are transmitted to the data processor where the data is analyzed. The cuvette after completion of measurement is removed from the detection unit 6 by a disposal mechanism (not shown), and discharged to a disposal container (not shown) provided below the measuring apparatus 1.

Figure 2:
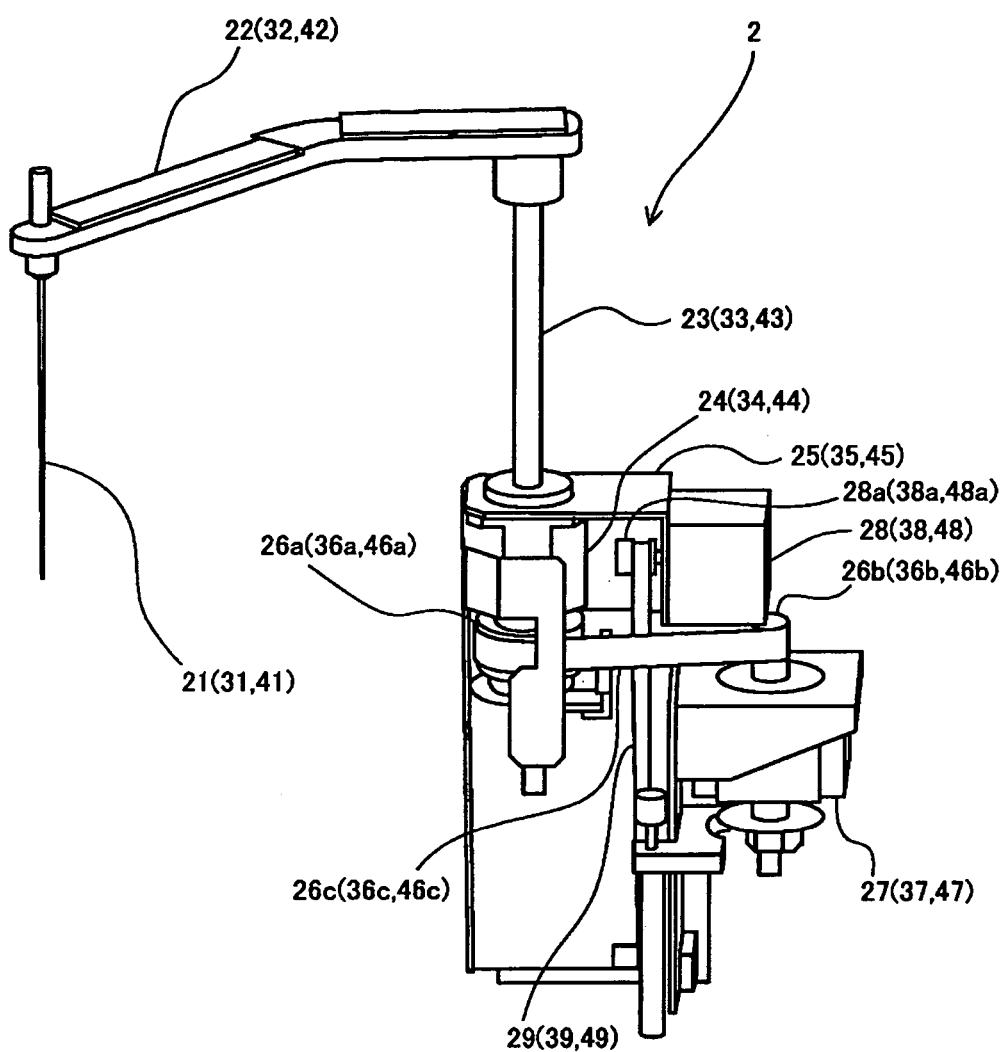
FIG. 2 is a perspective view showing a structure of an analyte dispensing arm unit belonging to a measuring apparatus of an embodiment.

Next, the arrangement of each unit will be explained in detail. FIG. 2 is a perspective view showing a structure of an analyte dispensing arm unit 2 (reagent dispensing arm units 3, 4) shown in FIG. 1. In this illustration, a structure of the analyte dispensing arm unit 2 will be explained based on FIG.

2. Since the reagent dispensing arm units 3, 4 have almost the same structure, an explanation of components in these units will be omitted while the reference numerals of such components are provided in parentheses led by corresponding components in the analyte dispensing arm unit. As shown in FIG. 2, the analyte dispensing arm unit 2 (reagent dispensing arm units 3, 4) has a needle-like pipette 21 (31, 41) extending in the vertical direction. The pipette 21 (31, 41) is formed into a tube having an internal cavity, and connected at its upper end with a fluid unit 8. This pipette 21 (31, 41) is attached to a distal end of an arm 22 (32, 42) in a substantially horizontal direction. A proximal end of the arm 22 (32, 42) is fixed to an upper end of a rotary shaft 23 (33, 43) extending in the vertical direction, and the arm 22 (32, 42) is allowed to oscillate by the rotary shaft 23 (33, 43) rotating about its center axis. The rotary shaft 23 (33, 43) is rotatably supported by a movement supporting member 24 (34, 44) moving in the vertical direction, and the movement supporting member 24 (34, 44) is attached to a pedestal 25 (35, 45) fixed to a frame (not shown) provided inside the measuring apparatus 1 in a vertically movable manner. To a lower end of the rotary shaft 23 (33, 43), a driven pulley 6*a* (36*a*, 46*a*) is coaxially fixed. To the movement supporting member 24 (34, 44), a stepping motor 27 (37, 47) whose output shaft 27*a* (37*a*, 47*a*) protrudes above is attached, and to this output shaft 27*a* (37*a*, 47*a*), a driving pulley 26*b* (36*b*, 46*b*) is coaxially fixed. A circular belt 26*c* (36*c*, 46*c*) is passed around the driving pulley 26*b* (36*b*, 46*b*) and the driven pulley 26*a* (36*a*, 46*a*) to allow transmission of a rotary motion of the output shaft 27*a* (37*a*, 47*a*) of the stepping motor 27 (37, 47) to the rotary shaft 2 (33, 43).

To the movement supporting member 24 (34, 44), also a stepping motor 28 (38, 48) is attached. The stepping motor 28 (38, 48) has an output shaft 28*a* (38*a*, 48*a*) extending horizontally. Below the stepping motor 28 (38, 48) of the movement supporting member 24 (34, 44), is a rotary shaft (not shown) parallel with the output shaft 28*a* (38*a*, 48*a*) of the stepping motor 28 (38, 48), and a circular belt 29 (39, 49) is passed across this rotary shaft and the output shaft 28*a* (38*a*, 48*a*). The belt 29 (39, 49) is partly fixed to the pedestal 25 (35, 45) (not shown), which allows the movement supporting member 24 (34, 44) to move vertically in accordance with the rotational direction of the output shaft 28*a* (38*a*, 48*a*) by operation of the stepping motor 28 (38, 48).

As the stepping motor 28 (38, 48) moves until the pipette 21 reaches above the analyte container, the arm 22 rotates in the horizontal direction about the rotary shaft 23, and by movement of the stepping motor 28 in the condition that the pipette 21 positioned above the analyte container, the movement supporting member 24 moves downward, and the pipette 21 is inserted inside the analyte container having an open upper part. When a tip end of the pipette 21 proceeds into the blood analyte, the movement supporting member 24 stops descending, and in this condition, the fluid unit operates to aspirate the blood analyte from the tip end of the pipette 21. Thereafter, the stepping motor 28 operates to move the movement supporting member 24 upward, and the pipette 21 moves above the analyte container. Further, the stepping motor 28 operates to cause the arm 22 to rotate in a horizontal direction about the rotary shaft 23, and the pipette 21 is positioned above the cuvette mounted to the position table unit 5. Then as the stepping motor 28 operates, the movement supporting member 24 moves downward to make the pipette 21 go into the cuvette whose upper end is open, and then the fluid unit 8 operates to discharge the blood analyte from the tip end of the pipette 21. After completion of discharging of the blood analyte, the stepping motor 28 operates to remove the pipette 21 upward from the interior of the cuvette.

Figure 8:
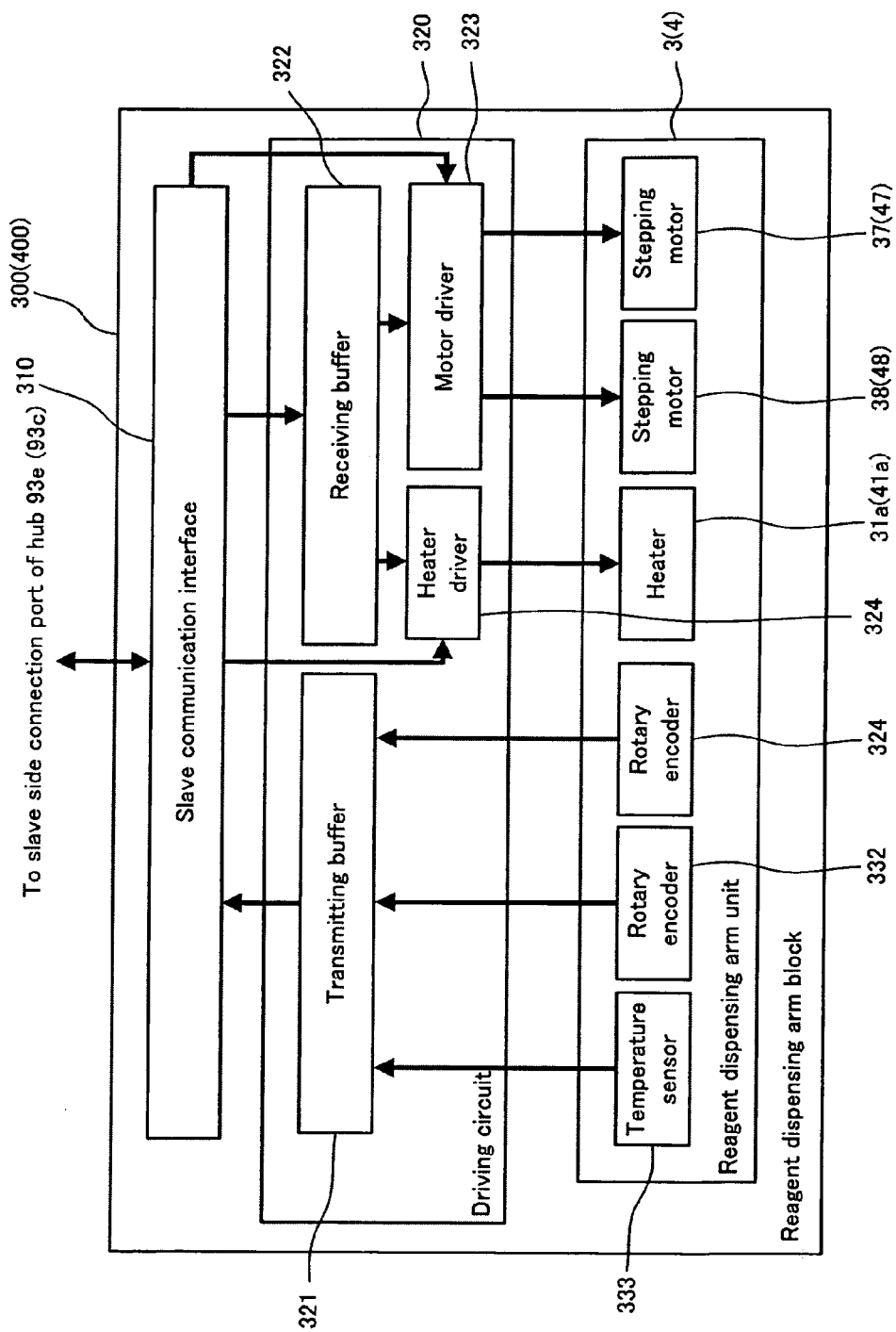
FIG. 8 is a block diagram showing a structure of a reagent dispensing arm block belonging to a measuring apparatus of an embodiment.

The pipettes 31, 41 of the reagent dispensing arm units 3, 4 are attached with heaters 31*a*, 41*a* to enable the aspirated reagents to be heated to a predetermined temperature (see FIG. 8). The reagent dispensing arm units 3, 4 also operate in a similar manner, and are able to aspirate the reagent in a reagent container and discharge the reagent into a cuvette set at a predetermined position.

Figure 3:
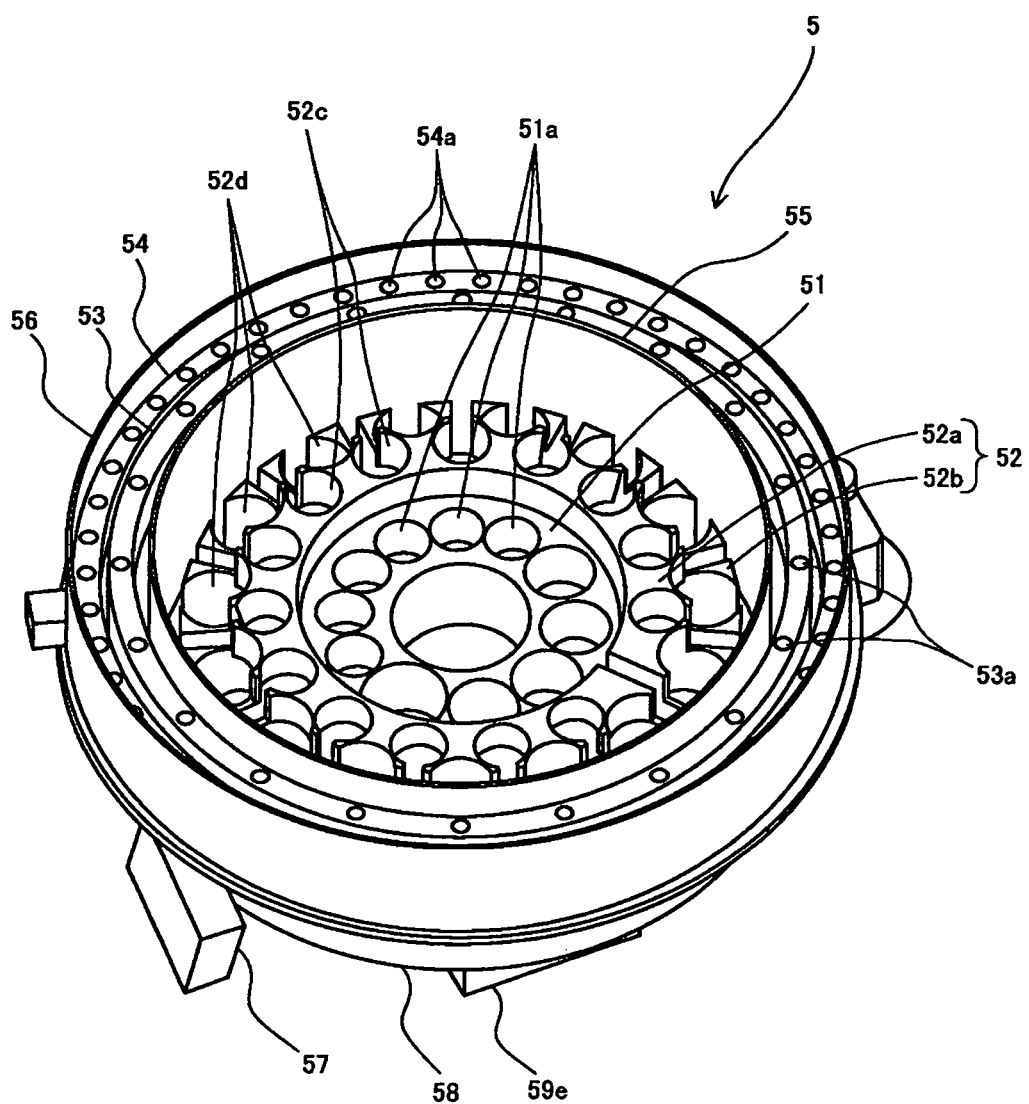
FIG. 3 is a perspective view showing a structure of a table unit belonging to a measuring apparatus of an embodiment.

FIG. 3 is a perspective view showing a structure of the table unit 5 shown in FIG. 1. As shown in FIG. 3, the table unit 5 has circular reagent tables 51, 52, and analyte tables 53, 54 which are provided coaxially with each other. The reagent table 51 has a plurality of cylindrical recesses 51*a* that are arranged in the circumferential direction, and each of the recesses 51*a* is designed to receive a reagent container in a detachable manner. The reagent table 52 is coaxially disposed outside the reagent table 51. The reagent table 52 includes an inner first reagent setting part 52*a* and an outside second reagent setting part 52*b*, wherein the inner first reagent setting part 52*a* is formed so as to be higher by one step than the outer second reagent setting part 52*b*. The first reagent setting part 52*a* and the second reagent setting part 52*b* each have a plurality of cylindrical recesses 52*c*, 52*d* arranged in the circumferential direction, and each of these recesses 52*c*, 52*d* is designed to receive a reagent container in a detachable manner. The cylindrical recesses 52*c*, 52*d* have a missing part located outside in the radial direction of the reagent table 52. Further, on a reagent container a barcode label is applied that bears a printed barcode showing the type or like of the reagent, and when a reagent container is set into the reagent tables 51, 52, it is set so that the barcode label faces outside in the radial direction of the reagent tables 51, 52. In the reagent container set in the reagent table 52, the barcode label is conveniently aligned with the missing part, so that the barcode label is exposed. This enables the barcode reader to read the barcode label as will be described later.

The analyte table 53 is coaxially provided outside the reagent table 52 via a circular intermediate wall 55. The analyte table 54 is coaxially provided outside the analyte table 53. The analyte tables 53, 54 each have a plurality of cylindrical recesses 53*a*, 54*a* arranged in the circumferential direction, and each of these recesses 53*a*, 54*a* is designed to receive a cuvette in a detachable manner. Outside of the analyte table 54 is covered with a circular outer wall 56. These analyte tables 53, 54 are positioned at higher levels than the reagent table 51, 52. To be more specific, in a bottom part of the table unit 5, the reagent tables 51, 52 protrude downward compared to the analyte table 53, 54. In a position below the analyte tables 53, 54 and beside the reagent tables 51, 52, a barcode reader 57 is provided. The bottom sides of the reagent tables 51, 52 and the analyte tables 53, 54 are covered with a cover 58, and to an upper end of the cover 58, the aforementioned outer 56 is attached. In proximity to the position where the barcode reader 57 is attached in the cover 58, a hole (not shown) is provided through which light emission from the barcode reader reaches reagent containers set in the reagent tables 51, 52. As described above, the recesses 52*c*, 52*d* of the reagent table 52 have a missing part and the light emission from the barcode reader 57 is exerted on a barcode label exposed from the missing part, which enables reading of the barcode by the barcode reader 57.

Figure 9:
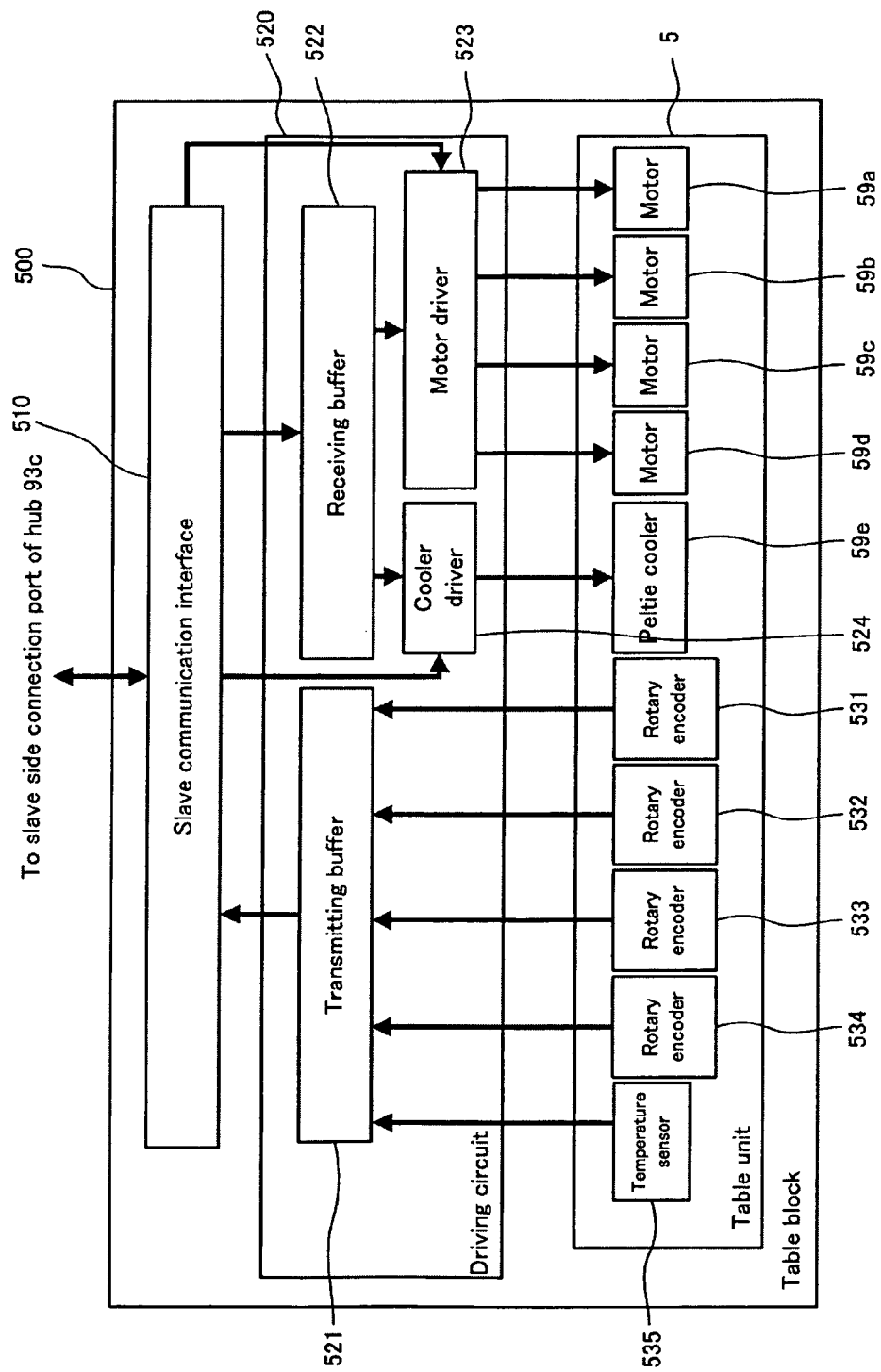
FIG. 9 is a block diagram showing a structure of a table block belonging to a measuring apparatus of an embodiment.

Although not illustrated in FIG. 3, below the analyte tables 53, 54, four stepping motors 59*a*, 59*b*, 59*c*, 59*d* are provided (see FIG. 9). The stepping motor 59*a* is connected to the reagent table 51 by a rotation transmission mechanism (not shown) composed of gears, and operation of the stepping motor 59a allows selective rotation of the reagent table 51 in either a forward or reverse direction. Similarly, each of the stepping motors 59b, 59c, 59d are respectively connected to the reagent table 51, and analyte tables 53, 54 by a rotation transmission mechanism composed of gears. With this arrangement, by operating the stepping motors 59a, 59b, 59c, 59d independently, it is possible to operate the reagent tables 51, 52 and the analyte tables 53, 54 independently.

Furthermore, below the reagent tables 51, 52, a Peltier cooler 59e is provided. This Peltier cooler 59e has a cooling surface attached to the bottom faces of the reagent tables 51, 52 via a heat conductive plate of metal or the like having a high heat conductivity, so that the reagent tables 51, 52 may be cooled by operation of the Peltier cooler 59e. By the intermediate wall 55 provided between the reagent tables 51, 52 and the analyte tables 53, 54, propagation of cooling effect by the Peltier cooler 59e is substantially blocked, so that the analyte tables 53, 54 will not be cooled by the Peltier cooler 59e. It is to be noted that the analyte tables 53, 54 and the reagent tables 51, 52 may be concurrently cooled by the Peltier cooler 59e, or other heat exchangers may be used as a cooling device in place of the Peltier cooler 59e without being limited to the arrangement described above.

Figure 4:
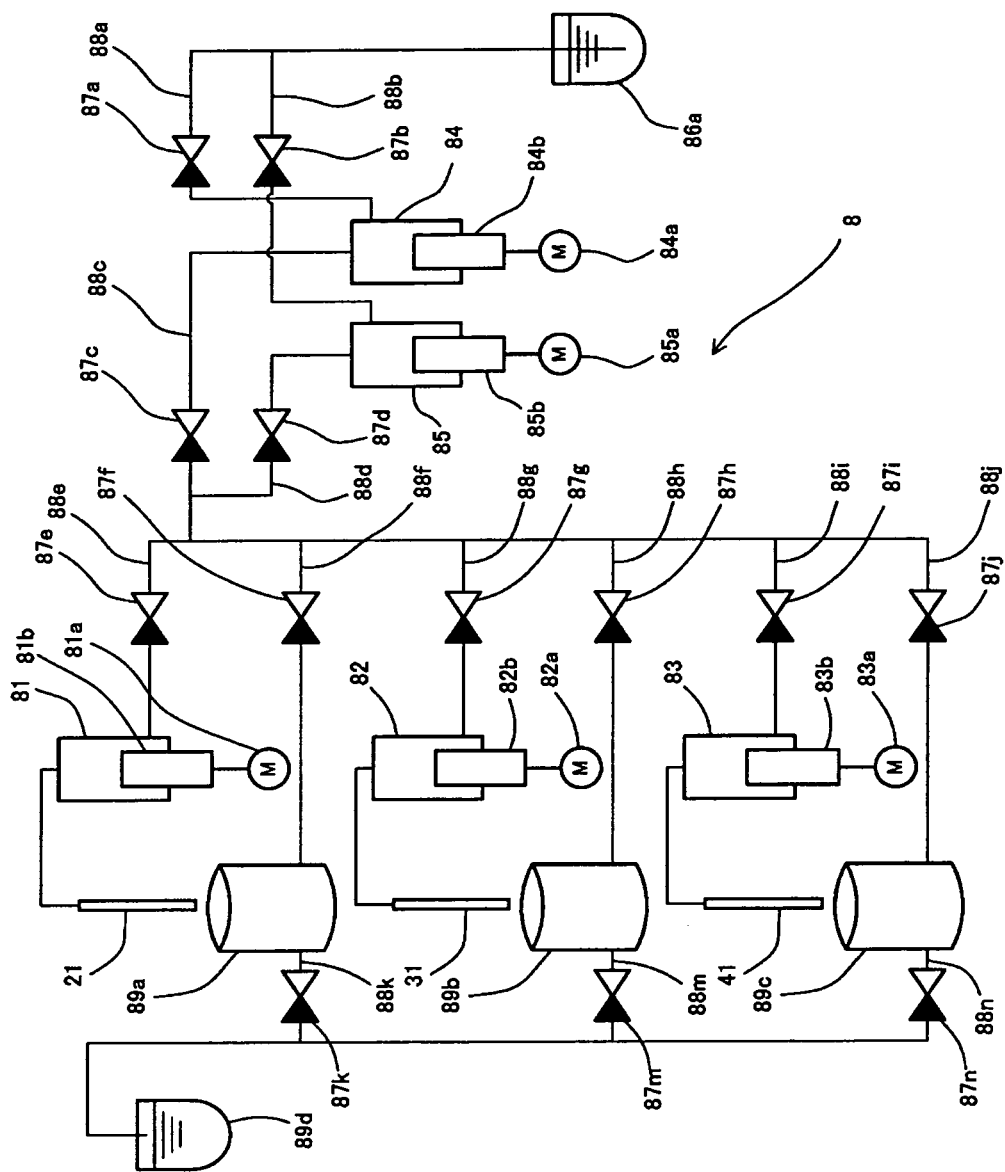
FIG. 4 is a fluid circuit diagram showing an overview of a fluid unit belonging to a measuring apparatus of an embodiment.

FIG. 4 is a fluid circuit diagram showing an overview of a fluid unit. As shown in FIG. 4, the fluid unit 8 is provided with five syringe pumps 81-85. The syringe pumps 81-85 are each attached with stepping motors 81a, 82a, 83a, 84a, 85a, respectively, and as the stepping motors 81a, 82a, 83a, 84a, 85a operate, the rotational motion thereof is converted into a linear motion and transmitted to the pistons 81b, 82b, 83b, 84b, 85b of the syringe pumps 81, 82, 83, 84, 85, and these pistons 81b, 82b, 83b, 84b, 85b are inserted into/removed from the respective cylinders.

The pipette 21 of the analyte dispensing arm unit 2 is connected to the syringe pump 81 via a tube for fluid communication, and is designed to aspirate or discharge an analyte according to operation of the syringe pumps 81. The pipette 31 of the reagent dispensing arm unit 3 is connected to the syringe pump 82 via a tube, and the pipette 41 of the reagent dispensing arm unit 4 is connected to the syringe pump 83 via a tube. As a result, the pipette 31 aspirates/discharges a reagent by operating the syringe pumps 83, and the pipette 41 aspirates/discharges a reagent by operating the syringe pumps 84.

The fluid unit 8 is also provided with a chamber 86a for pooling a cleaning solution, and the chamber 86a has a tube extending therefrom for feeding out a cleaning solution. This tube is branched in the midway such that one branch is connected to a connection port of a magnetic valve 87a and the other branch is connected to a connection port of a magnetic valve 87b. The magnetic valves 87a, 87b each are a dual-port magnetic valve. To the remaining port of the magnetic valve 87a, one end of a tube is connected, and the other end of the tube is connected to the syringe pump 84. Similarly, the remaining connection port of the magnetic valve 87b is connected to the syringe pump 85 by a tube. In this manner, the chamber 86a and the syringe pump 84 are connected with each other by a flow path 88a provided with the magnetic valve 87a in the midway; and the chamber 86a and the syringe pump 85 are connected with each other via a flow path 88b provided with the magnetic valve 87b in the midway. In the following description, a flow path is implemented by a tube for fluid communication, and a magnetic valve is implemented by a dual-port magnetic valve.

The syringe pump 84 is connected at its aspiration/discharge port with a flow path 88c provided with a magnetic valve 87c in the midway, and the syringe pumps 85 is connected at its aspiration/discharge port with a flow path 88d provided with a magnetic valve 87d in the midway. These flow paths converge, and then branch into six flow paths 88e, 88f, 88g, 88h, 88i, 88j. Three of these flow paths 88e, 88g, 88i are respectively connected with the syringe pumps 81, 82, 83. In the midway of the flow paths 88e, 88g, 88i, magnetic valves 87e, 87g, 87i are respectively provided.

To this fluid unit 8, washing units 89a, 89b, 89c are provided for washing the pipettes 21, 31, 41, respectively. The washing units 89a, 89b, 89c have a space for accommodating the pipettes 21, 31, 41, respectively, and each space has a spitting opening through which a cleaning solution is spit, and a discharge opening through which the cleaning solution is discharged. To a discharge opening of the washing unit 89a, the flow path 88f is connected, and to a discharge opening of the washing unit 89b, the flow path 88h is connected, and to a discharge opening of the washing unit 89c, the flow path 88j is connected. In the midway of the flow paths 88f, 88h, 88j, magnetic valves 87f, 87h, 87j are provided. As a result, each of the washing unit 89a, 89b, 89c spits out a cleaning solution through the spitting opening while accommodating the pipettes 21, 31, 41, respectively, which enables washing of the pipettes 21, 31, 41 from outside. After washing, a waste solution is discharged from a discharge opening.

From the discharge openings of the washing units 89a, 89b, 89c, flow paths 88k, 88m, 88n extend, and through these flow paths 88k, 88m, 88n, the converged path is connected to a chamber 89d for pooling a waste solution. In the midway of the flow path 88k, a magnetic valve 87k is provided, and similarly, in the midway of the flow paths 88m, 88n, magnetic valves 87m, 87n are provided.

In the case of washing the pipette 21 with such a structure, the fluid unit 8 is operated by the following procedure. First, the pipette 21 is moved and accommodated inside the washing unit 89a, and the cylinder of the syringe pump 81 is drawn to a predetermined position. Then the piston of the syringe pump 84 (or the syringe pump 8) is drawn in the condition that the magnetic valve 87a (or the magnetic valve 87b) is opened and the magnetic valve 87c (or the magnetic valve 87d) is closed, whereby a cleaning solution is aspirated from the chamber 86a. Thereafter, the magnetic valve 87a (or the magnetic valve 87b) is closed, and the magnetic valve 87c (or the magnetic valve 87d) is opened so as to open the magnetic valves 87e, 87f. At this time, the magnetic valves 87g-87j are closed, and the magnetic valve 87k is opened. In this condition, the piston of the syringe pump 84 (or the syringe pump 85) is caused to proceed to the depth of the cylinder. As a result, a cleaning solution communicates with the syringe pump 81 and the pipette 21 from the syringe pump 84 (or the syringe pump 85) via the flow path 88e, and discharged from the tip end of the pipette, whereby the interior of the pipette 21 is washed. The cleaning solution is spitted into the space of the washing unit 89a via the flow path 88f, whereby the exterior of the pipette 21 is washed. A waste solution generated as a result of washing is discharged into the chamber 89d via the flow path 88m. In the case of washing the pipette 31, the pipette 31 is moved inside the washing unit 89b, and the magnetic valves 87g, 87h, 87m in place of the magnetic valves 87e, 87f, 87k are opened when discharging a cleaning solution from the syringe pump 84 (or the syringe pump 85); and in the case of washing the pipette 31, the pipette 31 is moved inside the washing unit 89c, and the magnetic valves 87i, 87j, 87n in place of the magnetic valves 87e, 87f, 87k are opened when discharging a cleaning solution from the syringe pump 84 (or the syringe pump 85).

Figure 5:
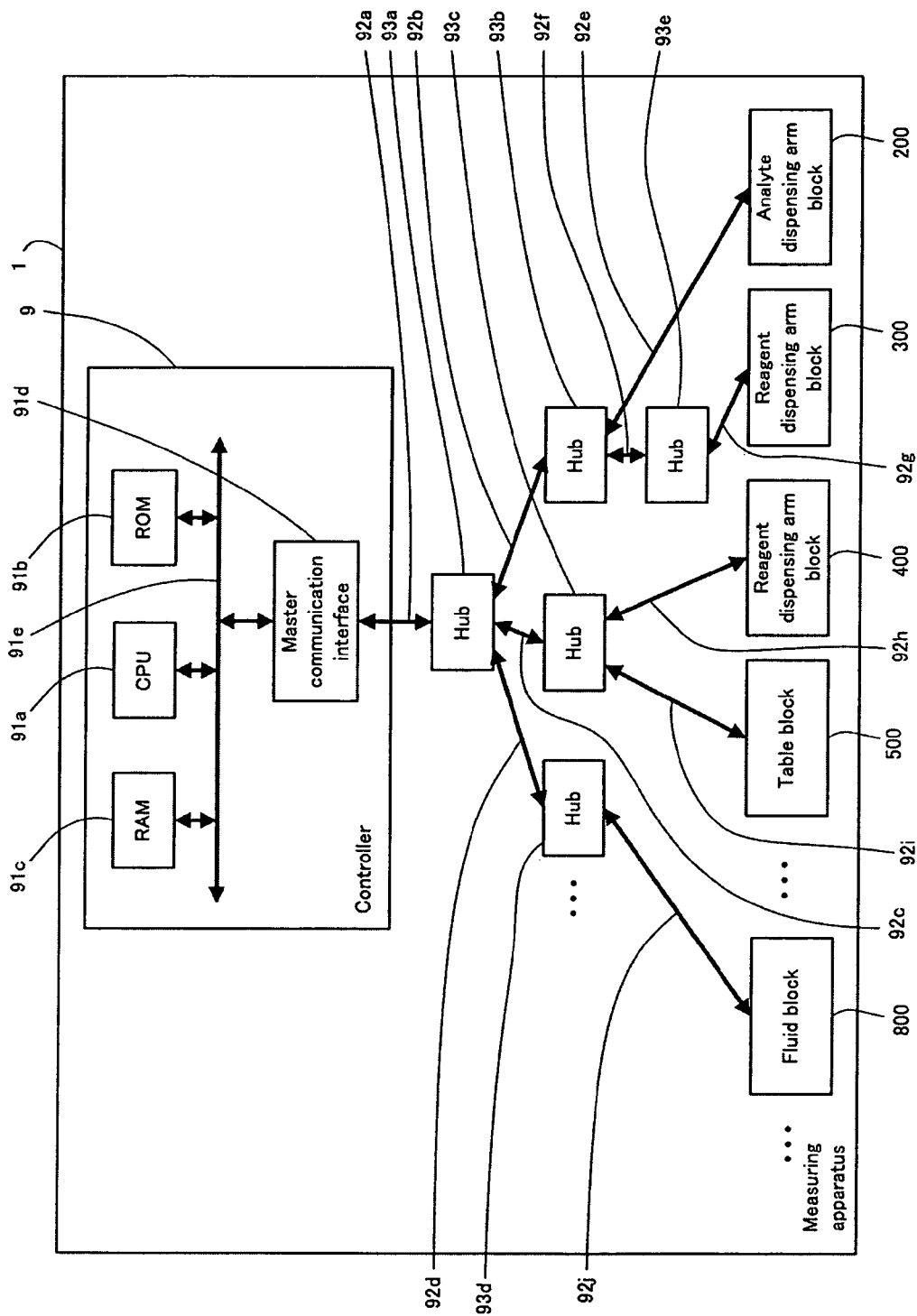
FIG. 5 is a block diagram showing a connection relationship between a controller and each mechanism unit of a measuring apparatus of an embodiment.

Operations of such mechanism units as described above, including the analyte dispensing arm unit 2, the reagent dispensing arm units 3, 4, the table unit 5 and the fluid unit 8 are controlled by a controller 9 will be illustrated below. FIG. 5 is a block diagram showing a connection relationship between the controller 9 of the measuring apparatus 1 and each mechanism unit. As shown in FIG. 5, the controller 9 includes a CPU 91a, a ROM 91b, a RAM 91c, and a master communication interface 91d. The CPU 91a is able to execute a computer program stored in the ROM 91b and a computer program loaded to the RAM 91c. The ROM 91b is implemented by a mask ROM, PROM, EPROM, EEPROM or the like, and stores a computer program executed by the CPU 91a and data used for the computer program. The RAM 91c is implemented by a SRAM, DRAM or the like. The RAM 91c is used as a work area of the CPU 91a during execution of a computer program stored in the ROM 91b.

As shown in FIG. 5, the CPU 91a is connected to the ROM 91b, the RAM 91c, and the master communication interface 91d via a data communication bus 91e. As will be explained in detail later, each mechanism unit 2, 3, 4, 5, 6, 7 is individually accompanied by a slave communication interface and a driving circuit. To be more specific, the analyte dispensing arm unit 2 is accompanied by a slave communication interface 210 and a driving circuit 220 (see FIG. 7), the reagent dispensing arm unit 3 is accompanied by a slave communication interface 310 and a driving circuit 320 (see FIG. 8). The same applies to other mechanism units 4, 5, 6, 7, 8, . . . . In this manner, a functional block is constructed by a slave communication interface, a driving circuit and a mechanism unit. In other words, an analyte dispensing arm block 200 which is a functional group (see FIG. 7) is constructed by the analyte dispensing arm unit 2, the slave communication interface 210 and the driving circuit 220; and a reagent dispensing arm block 300 which is a functional group (see FIG. 8) is constructed by the reagent dispensing arm unit 3, the slave communication interface 310 and the driving circuit 320. Similarly, the reagent dispensing arm unit 4, the table unit 5, and the fluid unit 8 respectively constitute a reagent dispensing arm block 400, a table block 500, a fluid block 800 together with a slave communication interface and a driving circuit, and also the detection unit 6, the conveyance unit 7, and other mechanism units respectively constitute functional blocks together with a slave communication interface and a driving circuit, although illustration thereof is omitted herein.

The master communication interface 91d is a serial communication interface for allowing communication between each of the functional blocks 200, 300, 400, 500, . . . , 800, . . . and the CPU 91a, and is designed to conduct packet communication with a slave communication interface as will be described later. From this master communication interface 91d, a signal transmission cable 92a for data communication with respect to each of the functional blocks 200, 300, 400, 500, . . . , 800, . . . is provided in an extended manner. To this signal transmission cable 92a, a hub 93a for communication relay is connected. The hub 93a is provided with one master side connection port 101 and a plurality of slave side connection ports 102a, 102b, 102c, 102d, . . . (see FIG. 6). The above described signal transmission cable 92a is connected to the master side connection port 101. To the three slave side connection ports of the hub 93a, one end of three signal transmission cables 92b, 92c, 92d are respectively connected, and the other ends of the three signal transmission cables 92b, 92c, 92d are respectively connected to master side connection ports of hubs 93b, 93c, 93d. To one slave side connection port of the hub 93b, a signal transmission cable 92e is connected, and the signal transmission cable 92e is connected to the analyte dispensing arm block 200. That is, the controller 9 and the analyte dispensing arm block 200 are connected while relayed by two hubs 93a, 93b.

Further, the other one slave side connection port of the hub 93b is connected to a master side connection port of the hub 93e via a signal transmission cable 92f, and one slave side connection port of the hub 93e is connected to the reagent dispensing arm block 300 via a signal transmission cable 92g. In this manner, the controller 9 and the reagent dispensing arm block 300 are connected with each other while relayed by the three hubs 93a, 93b, 93e.

Further, one slave side connection port of the hub 93c is connected to the reagent dispensing arm block 400 via a signal transmission cable 92h, and the other slave side connection port of the hub 93c is connected to the table block 500 via a signal transmission cable 92i. Further, one slave side connection port of the hub 93d is connected to the fluid block 800 via a signal transmission cable 92j. That is, the controller 9 is connected to the reagent dispensing arm block 400 and the table block 500 while relayed by the hubs 93a, 93c, respectively, and connected to the fluid block 800 while relayed by the hubs 93a, 93d. As described above, the hubs 93a-93e are used for relaying communication between the controller 9 and the functional blocks 200, 300, 400, 500, . . . , 800, . . . , and the relay between the controller 9 and the functional blocks 200, 300, 400, 500, . . . , 800, . . . may be achieved by one hub or a plurality of hubs.

Further, as described above, the hubs 93a-93e have one master side connection port 101 and a plurality of slave side connection ports 102a, 102b, 102c, 102d, . . . , and the master side connection port 101 is usually connected to a device (controller 9, or other hub) on the command transmitting side, namely on the side of the controller 9, and the slave side connection ports 102a, 102b, 102c, 102d, . . . are usually connected to a device (functional block or other hub) of command the receiving side, namely on the side of the functional block. That is, by connecting the controller 9 to each of the functional blocks 200, 300, 400, 500, . . . , 800, . . . , via the hubs 93a-93e rather than directly, it is possible to connect the controller 9 to the plurality of functional blocks 200, 300, 400, 500, . . . , 800, . . . , even when the controller 9 has only one connection port. In other words, there is no need to design the controller 9 so as to have a number of connection ports corresponding to the number of functional blocks. Furthermore, connection in a tree structure from the controller 9 as a route node enables various connection forms even when the same number of functional blocks are connected, so that the flexibility of the connection form is improved.

Figure 6:
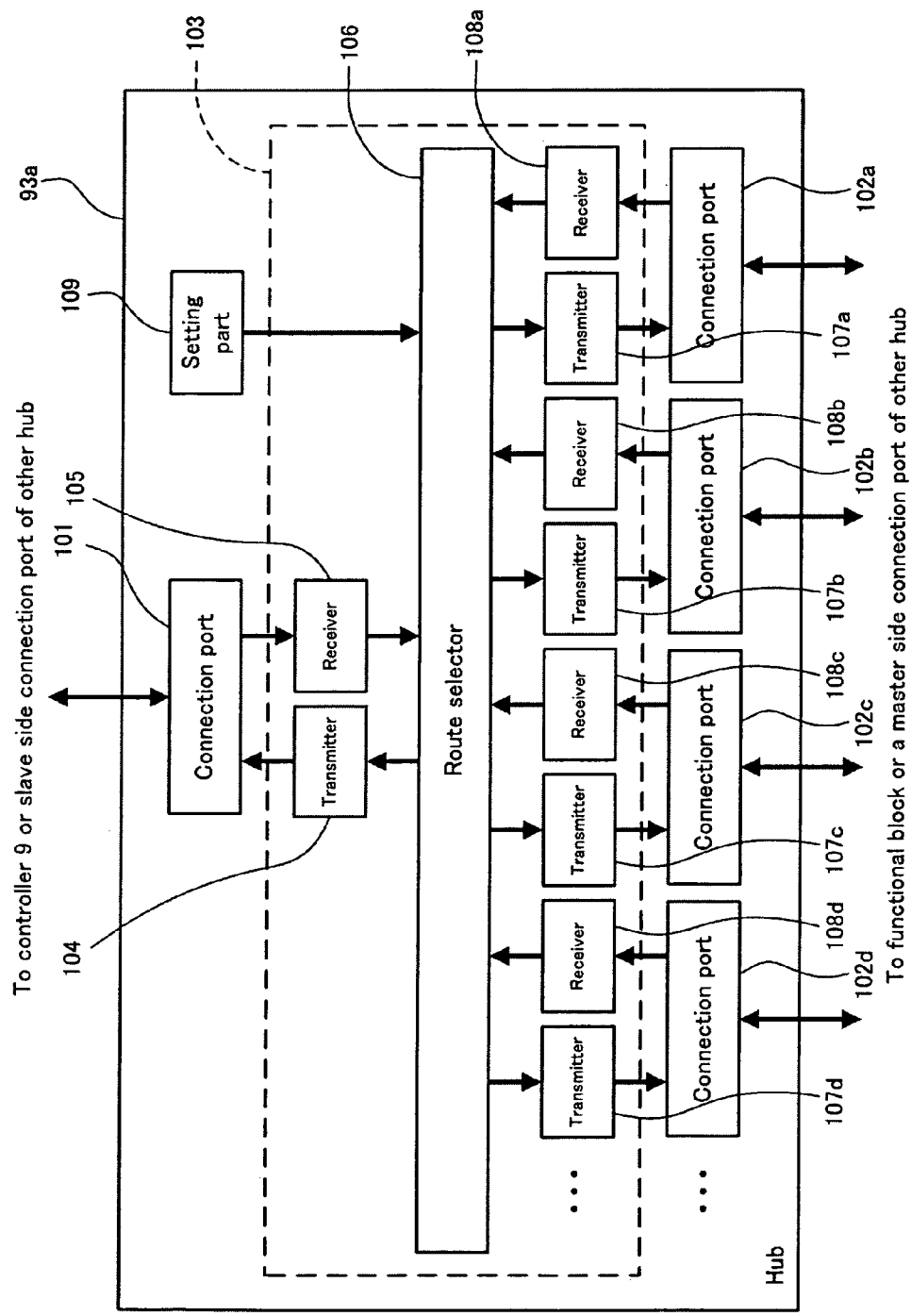
FIG. 6 is a block diagram showing an arrangement of hubs belonging to a measuring apparatus of an embodiment.

Next, a structure of hub will be explained in detail. FIG. 6 is a block diagram showing a structure of a hub. As shown in FIG. 6, the hub 93a has one master side connection port 101 and a plurality of slave side connection ports 102a, 102b, 102c, 102d, . . . . As described above, the connection port 101 is connected to the controller 9 or a slave side connection port of other hub via a signal transmission cable, and the connection ports 102a, 102b, 102c, 102d, . . . are connected to a functional block or a master side connection port of other hub via a signal transmission cable. To these connection ports 101, 102a, 102b, 102c, 102d, . . . , a communication circuit 103 implemented by e.g., FPGA or ASIC is connected via an electric signal line. The communication circuit 103 is provided as partial circuits with a transmitter 104 and a receiver 105 of master side, a route selector 106, transmitters 107a, 107b, 107c, 107d, . . . and receivers 108a, 108b, 108c, 108d, . . . of slave side. The connection port 101 is connected with the transmitter 104 and the receiver 105 in a communicable manner. Such transmitter 104 and receiver 105 each have a transmitting buffer and a receiving buffer, and data stored in the transmitting buffer is externally transmitted through the connection port 101 of the master side, and the data transmitted to the connection port 101 of the master side is written in the receiving buffer. Further, the connection ports 102*a*, 102*b*, 102*c*, 102*d*, . . . are respectively connected to the transmitters 107*a*, 107*b*, 107*c*, 107*d*, . . . and the receiver 108*a*, 108*b*, 108*c*, 108*d*, . . . in a communicable manner. Such transmitters 107*a*, 107*b*, 107*c*, 107*d*, . . . also have a transmitting buffer as is the case with the transmitter 104, and the receivers 108*a*, 108*b*, 108*c*, 108*d*, . . . , also have a receiving buffer as is the same with the receiver 105, and data stored in a transmitting buffer of the transmitter 107*a* (107*b*, 107*c*, 107*d*, . . . ) is externally transmitted through the connection port 102*a* (102*b*, 102*c*, 102*d*, . . . ) of the slave side, and the data transmitted to the connection port 102*a* (102*b*, 102*c*, 102*d* . . . ) on the slave side is written into the receiving buffer of the data receiver 108*a* (108*b*, 108*c*, 108*d*, . . . ).

The transmitter 104 and the receiver 105 on the master side and the transmitters 107*a*, 107*b*, 107*c*, 107*d*, . . . and the receivers 108*a*, 108*b*, 108*c*, 108*d*, . . . on the slave side are respectively connected to the route selector 106. To the route selector 106, a setting part 109 such as a dip switch provided outside the communication circuit 103 is connected in such a manner that a user may set the number of stages of the hub from the master side, the order of the hub from the controller 9 with the use of the setting part 109. The route selector 106 reads out from the receiver 105 a packet transmitted to a functional block from the controller 9, and extracts an address corresponding to a setting value of the setting part 109 from the packet, interprets the address and selects a transmitter to which the addressed functional block is connected from the transmitters 107*a*, 107*b*, 107*c*, 107*d*, . . . , and writes the packet to the selected transmitter. As to a packet transmitted from a functional block, any packet is addressed to the controller 9, there is no need to carry out route distribution. Accordingly, the route selector 106 directly writes a packet read out from the receiver 108*a*, 108*b*, 108*c*, 108*d*, . . . to the transmitter 104 without conducting analysis.

Figure 7:
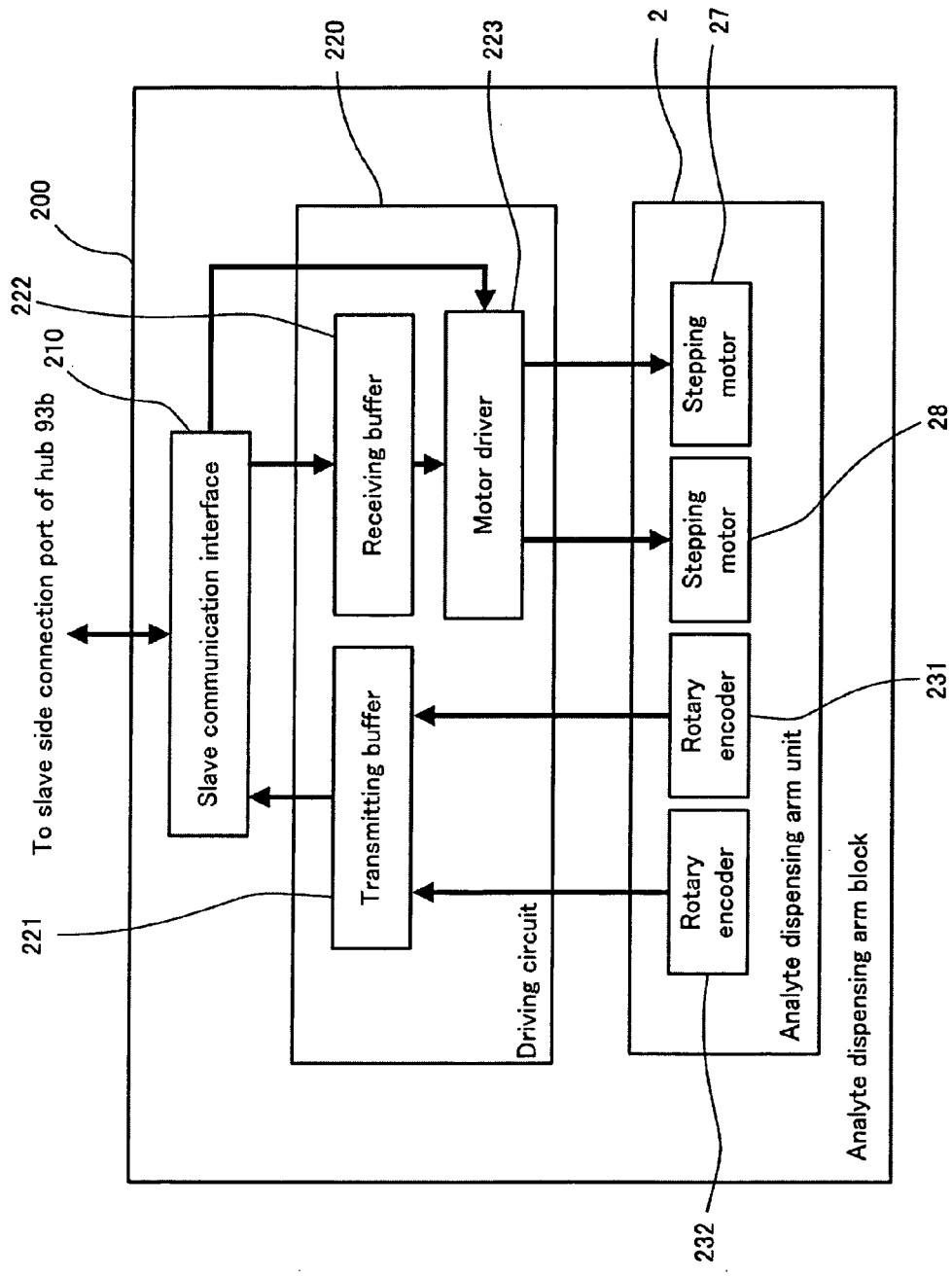
FIG. 7 is a block diagram showing a structure of an analyte dispensing arm block belonging to a measuring apparatus of an embodiment.

Next, a structure of each functional block will be explained. FIG. 7 is a block diagram showing a structure of the analyte dispensing arm block 200. As shown in FIG. 7, the analyte dispensing arm block 200 includes the analyte dispensing arm unit 2, the slave communication interface 210, and the driving circuit 220. The slave communication interface 210 is a communications interface for communication with the controller 9, and connected with the signal transmission cable 92*e* connected to the slave side connection port of the hub 93*b*. An address for identifying the functional block 200 is assigned to the slave communication interface 210, and the controller 9 is able to identify the analyte dispensing arm block 200 from this address and transmit data. The slave communication interface 210 is connected to the driving circuit 220 so as to allow mutual data communication. The driving circuit 220 has a transmitting buffer 221, a receiving buffer 222, and a motor driver 223. The transmitting buffer 221 is a buffer for storing data transmitted to the controller 9 from the analyte dispensing arm block 200, and the receiving buffer 222 is a buffer for receiving and storing data from the controller 9. Data written into the transmitting buffer 221 is read out by the slave communication interface 210 and transmitted to the controller 9, and the data received by the slave communication interface 210 from the controller 9 is written into the data receiving buffer 222. Data written into the receiving buffer 222 is given to the motor driver 223. The motor driver 223 is a circuit capable of driving a stepping motor, and is able to directly (without intervention by the receiving buffer 222) to accept an operation starting instruction from the slave communication interface 210. Upon acceptance of such an operation starting instruction from the slave communication interface 210, the motor driver 223 reads out the data transmitted from the controller 9 from the receiving buffer 222, and individually drives the stepping motors 27, 28 according to the control data.

The analyte dispensing arm unit 2 is provide with a rotary encoder 231 capable of detecting a rotation angle of the stepping motor 27 and a rotary encoder 232 capable of detecting a rotation angle of the stepping motor 28. The rotary encoders 231, 232 are respectively connected to the driving circuit 220 via an electric signal line, and output data of the rotary encoders 231, 232 is written into the transmitting buffer 221 every determined sampling cycle. The slave communication interface 210 reads out detection data of the rotary encoders 231, 232 stored in the transmitting buffer 221 at an appropriate timing, and transmits the same to the controller 9.

Next, an explanation will be provided regarding a structure of the reagent dispensing arm blocks 300, 400. FIG. 8 is a block diagram showing a structure of the reagent dispensing arm block 300 (400). As shown in FIG. 8, the reagent dispensing arm block 300 (400) includes the reagent dispensing arm unit 3 (4), the slave communication interface 310 and the driving circuit 320. An address for identifying the reagent dispensing arm block 300 (400) is assigned to the slave communication interface 310. The remaining structure of the slave communication interface 310 is as same as that of the slave communication interface 210 of the analyte dispensing arm block 200, and hence explanation thereof will be omitted. The driving circuit 320 includes a transmitting buffer 321, a receiving buffer 322, a motor driver 323, and a heater driver 324. Structures of the transmitting buffer 321, the receiving buffer 322, and the motor driver 323 are as same as those of the transmitting buffer 221, the receiving buffer 222 and the motor driver 223 of the analyte dispensing arm block 200, and hence explanation thereof will be omitted. The heater driver 324 is a circuit capable of driving a heater 31*a* and reading out data stored in the receiving buffer 322, and is able to directly accept an operation starting instruction from the slave communication interface 310. Upon reception of an operation starting instruction from the slave communication interface 310, the heater driver 324 reads out control data transmitted from the controller 9 from the receiving buffer 322, and drives the heater 31*a* (41*a*) in accordance with the control data.

The reagent dispensing arm unit 3 (4) is provided with a rotary encoder 331 capable of detecting a rotation angle of the stepping motors 37 (47), and a rotary encoder 332 capable of detecting a rotation angle of the stepping motor 38 (48), and also provided with a thermocouple capable of detecting temperature of the heater 31*a* (41*a*), and a temperature sensor 333 such as a thermistor. The rotary encoders 331, 332 and the temperature sensor 333 are respectively connected to the driving circuit 320 via an electric signal line, and output data of the rotary encoders 331, 332 and the temperature sensor 333 are written into the transmitting buffer 321 every predetermined sampling cycle. The slave communication interface 310 reads out detection data of the rotary encoders 331, 332 and the temperature sensor 333 stored in the transmitting buffer 321 in appropriate timing, and transmits it to the controller 9.

A structure of the table block 500 will now be provided. FIG. 9 is a block diagram showing a structure of the table block 500. As shown in FIG. 9, the table block 500 includes the table unit 5, a slave communication interface 510, and a driving circuit 520. To the slave communication interface 510, an address for identifying the table block 500 is assigned. The remaining structure of the slave communication interface 510 is the same as that of the slave communication interface 210 of the analyte dispensing arm block 200, and hence explanation thereof will be omitted.

The driving circuit 520 includes a transmitting buffer 521, a receiving buffer 522, a motor driver 523, and a cooler driver 524. Structures of the transmitting buffer 521 and the receiving buffer 522 are similar to those of the transmitting buffer 221 and the receiving buffer 222 of the analyte dispensing arm block 210, and hence explanation thereof will be omitted. The motor driver 523 is a circuit capable of driving a stepping motor, and connected to the stepping motors 59a, 59b, 59c, 59d of the table unit 5. The motor driver 523 is able to read out data stored in the receiving buffer 522 and accept an operation starting instruction from the slave communication interface 510, and upon reception of an operation starting instruction, it reads out control data transmitted from the controller 9 from the receiving buffer 522 and drives the three stepping motors 59a, 59b, 59c, 59d in accordance with the control data.

Further, the cooler driver 524 is a circuit capable of driving the Peltier cooler 59e and is able to read out data stored in the receiving buffer 522 and directly accept an operation starting instruction from the slave communication interface 510. Upon acceptance of an operation starting instruction from the slave communication interface 510, the cooler driver 524 reads out from the receiving buffer 522 control data transmitted from the controller 9, and drives the Peltier cooler 59e in accordance with the control data.

The table unit 5 is provided with rotary encoders 531, 532, 533, 534 capable of detecting a rotational angle of the stepping motors 59a, 59b, 59, 59d, a thermocouple capable of detecting temperature of the Peltier cooler 59e, and a temperature sensor 535 such as thermistor. The rotary encoders 531, 532, 533, 534 and the temperature sensor 535 are respectively connected to the driving circuit 520 via an electric signal line, and output data of the rotary encoders 531, 532, 533, 534 and the temperature sensor 535 are written into the transmitting buffer 521 every predetermined sampling cycle. The slave communication interface 510 reads out detection data of the rotary encoder 531, 532, 533, 534 and the temperature sensor 535 stored in the transmitting buffer 521 in appropriate timing, and transmits it to the controller 9.

Figure 10:
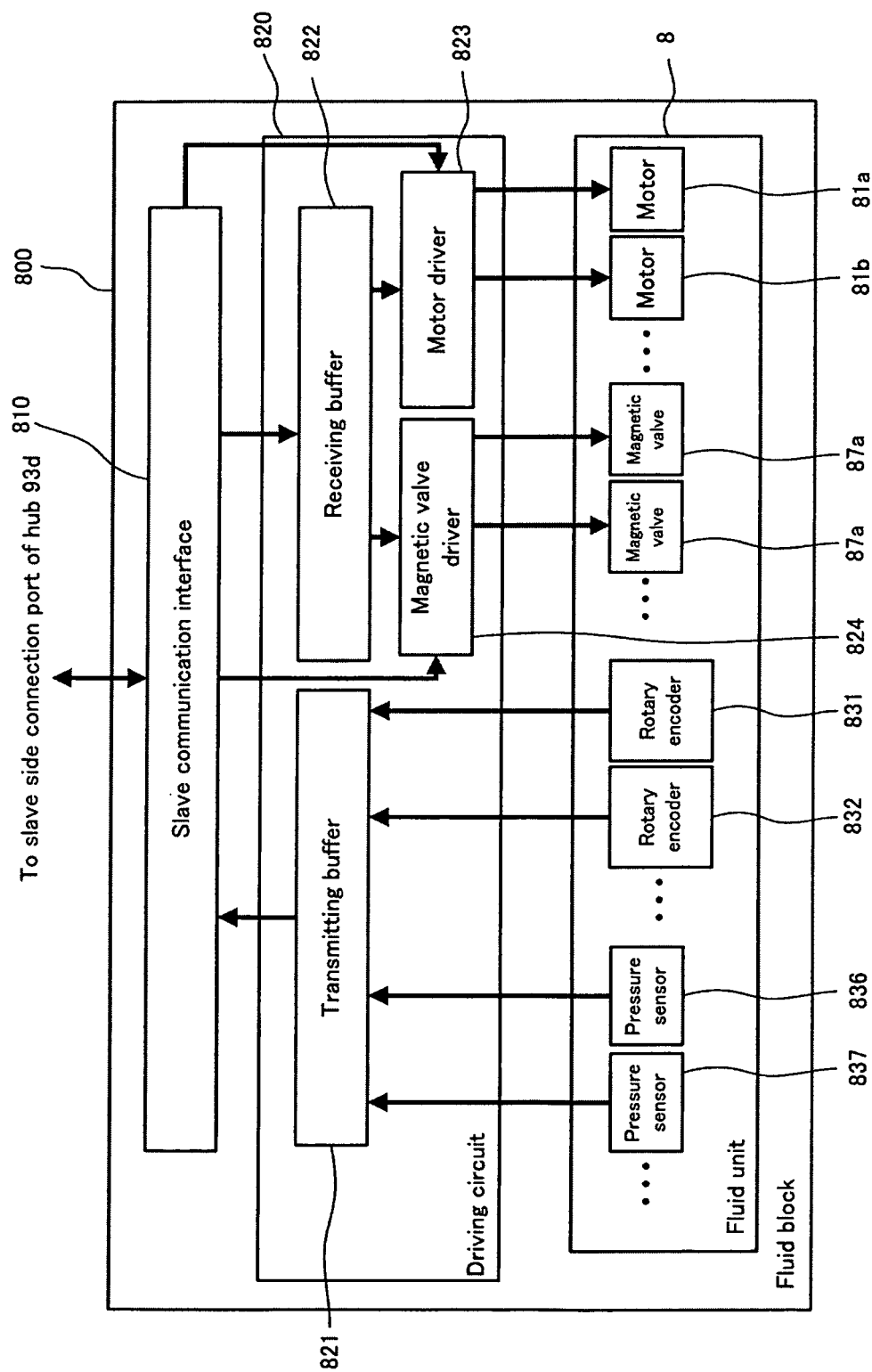
FIG. 10 is a block diagram showing a structure of a fluid block.
Figure 11:
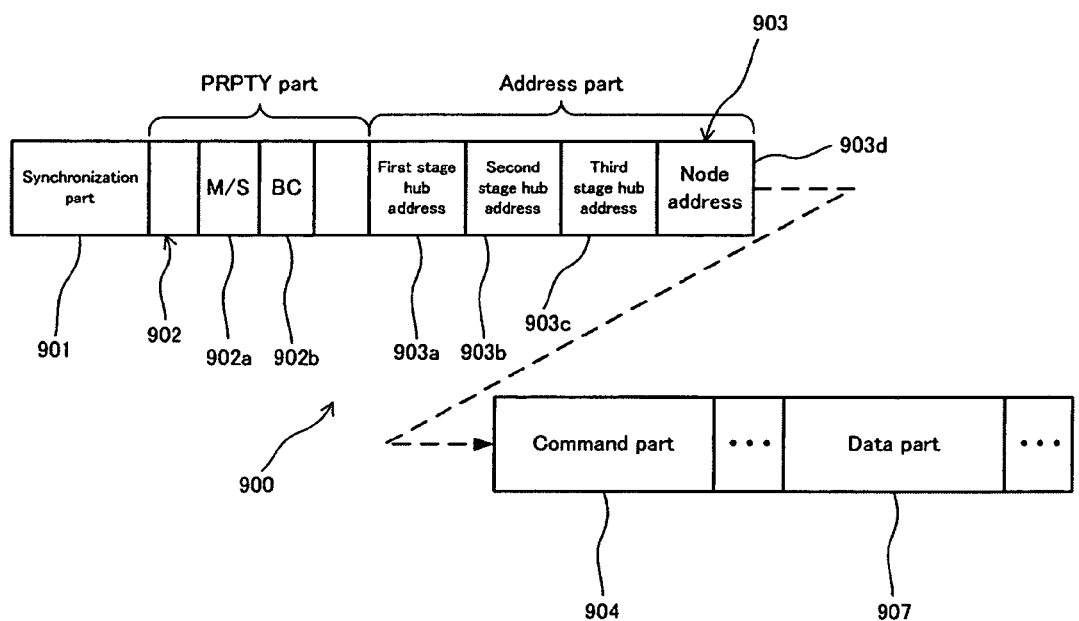
FIG. 11 is a schematic view showing a structure of a transmission packet.

Next, a structure of the fluid block 800 will be provided. FIG. 10 is a block diagram showing a structure of the fluid block 800. As shown in FIG. 11, the fluid block 800 includes the fluid unit 8, a slave communication interface 810, and a driving circuit 820. An address for identifying the fluid block 800 is assigned to the slave communication interface 810. The remaining structure of the slave communication interface 810 is similar to that of the slave communication interface 210 of the analyte dispensing arm block 200, and hence explanation thereof will be omitted. The driving circuit 820 includes a transmitting buffer 821, a receiving buffer 822, a motor driver 823, and a magnetic valve driver 824. Structures of the transmitting buffer 821 and the receiving buffer 822 are similar to those of the transmitting buffer 221 and the receiving buffer 222 of the analyte dispensing arm block 200, and hence explanation thereof will be omitted. The motor driver 823 is a circuit capable of driving a stepping motor, and is connected to the stepping motors 81a, 82a, 83a, 84a, 85a of the fluid unit 8 via an electric signal line. The motor driver 823 is able to read out data stored in the receiving buffer 822 and directly accept an operation starting instruction from the slave communication interface 810. Upon acceptance of the operation starting instruction, the motor driver 823 reads out from the receiving buffer 822 control data transmitted from the controller 9, and individually drives the stepping motors 81a, 82a, 83a, 84a, 85a according to the control data.

The magnetic valve driver 824 is a circuit capable of driving the magnetic valves 87a, 87b, 87c, 87d, 87e, 87f, 87g, 87h, 87i, 87j, 87k, 87m, 87n and is able to read out data stored in the receiving buffer 822 and directly accept an operation starting instruction from the slave communication interface 810. Upon acceptance of an operation starting instruction from the slave communication interface 810, the magnetic valve driver 824 reads out from the receiving buffer 822 control data transmitted from the controller 9, and drives the magnetic valves 87a, 87b, 87c, 87d, 87e, 87f, 87g, 87h, 87i, 87j, 87k, 87m, 87n in accordance with the control data.

The table unit 5 is provided with rotary encoders 831, 832, ..., capable of individually detecting a rotation angle of the stepping motors 81a, 82a, 83a, 84a, 85a and a plurality of pressure sensors 836, 837, ... disposed in a flow path. The rotary encoders 831, 832, 833, 834, 835 and the pressure sensors 836, 837, ... are respectively connected to the driving circuit 820 via an electric signal line, and output data of the rotary encoders 831, 832, ... and the pressure sensors 836, 837, ... are written into a transmitting buffer 821 every predetermined sampling cycle. The slave communication interface 81 reads out detection data of the rotary encoders 831, 832, ... and the pressure sensors 836, 837, ... stored in the transmitting buffer 821 in appropriate timing, and transmits it to the controller 9.

Next, the structure of a packet transmitted to a functional block from the controller 9 will be explained. FIG. 11 is a schematic view showing a structure of a packet for transmission. A packet 900 includes a plurality of segments: a synchronization part 901, a PRPTY part 902, an address part 903, a command part 904, and a data part 907 in this order from the head of the packet. The synchronization part 901 is a segment indicating start of the packet 900, and the hubs 93a-93e and the salve communication interfaces 210, 310, 410, 510, ... start receiving the packet 900 upon detection of this segment.

The PRPTY part 902 is a segment for data for designating a communication direction (a direction from the controller 9 to a functional block or a direction from a functional block to the controller 9), and for designating broadcasting (communication directed to every function block 200, 300, 400, 500,) or unicasting (communication directed to a specific functional block). Concretely, the PRPTY part 902 includes an M/S bit 902a and a BC bit 902b. When the M/S bit 902a is "1", it is meant that the packet is directed to a functional block from the controller 9, and when the M/S bit 902a is "0", it is meant that the packet is directed from a functional block to the controller 9. When the BC bit 902b is "1", it is meant that the communication is broadcasting, and when the BC bit 902b is "0", it is meant that the communication is unicasting.

Figure 12:
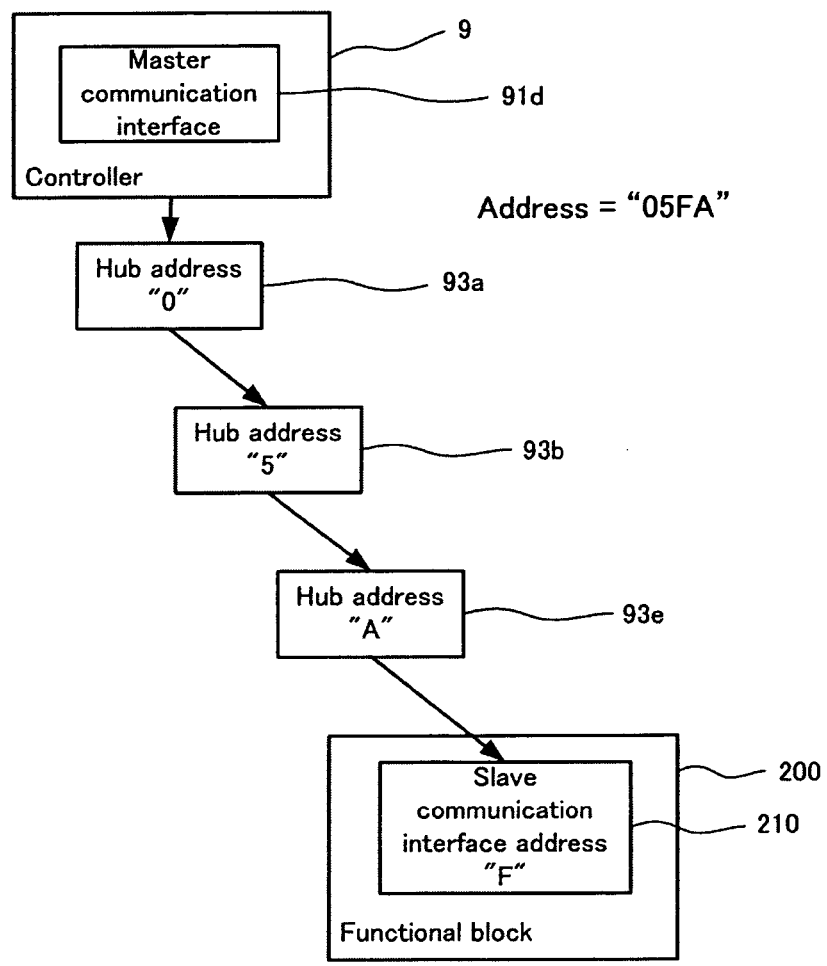
FIG. 12 is a view showing the architecture of the address designation of a packet.
Figure 13:
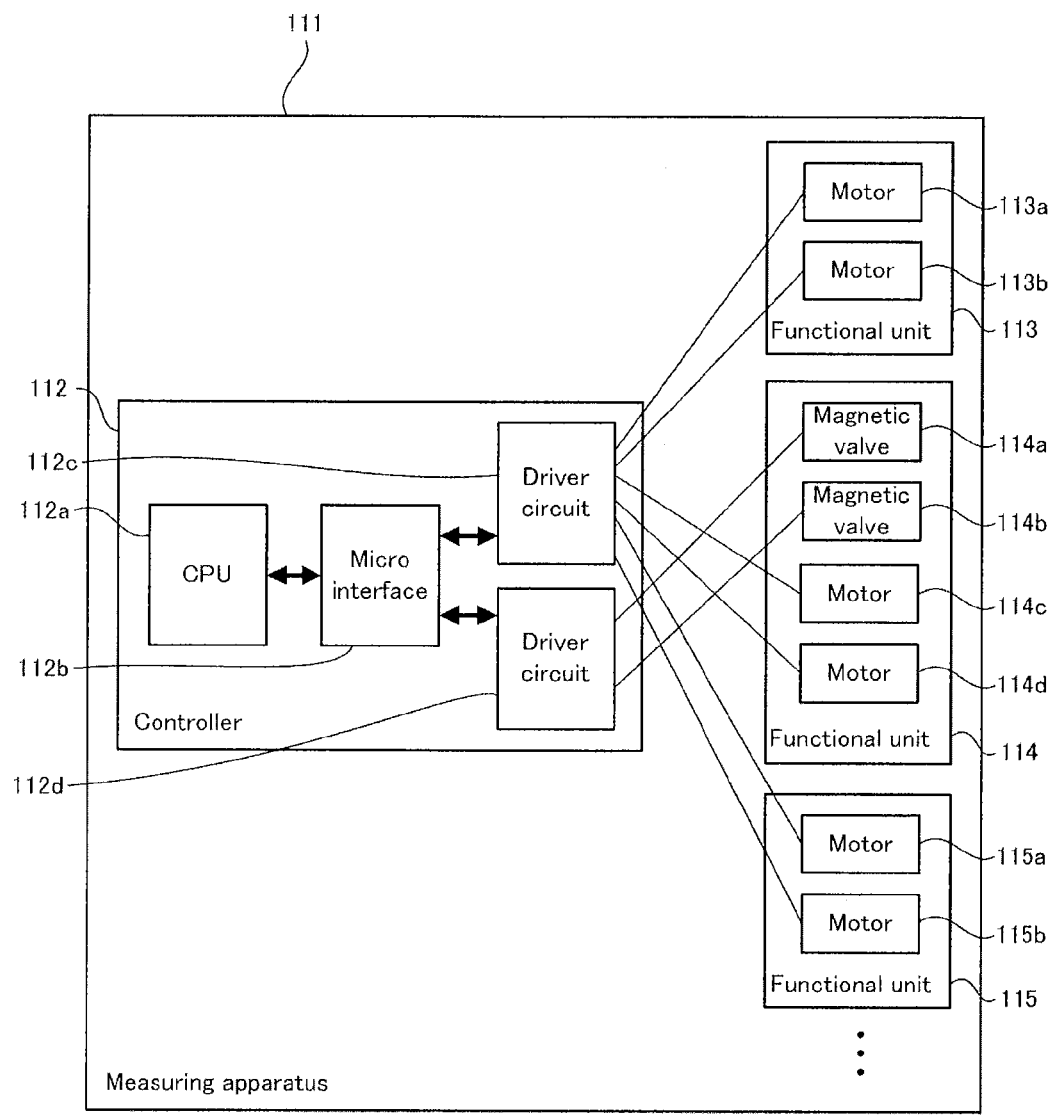
FIG. 13 is a block diagram showing the structure of a conventional measuring apparatus.

The address part 903 is a segment of address for a device that receives the packet 900. FIG. 12 is a view showing a structure of address designation of the packet. As shown in FIG. 12, the address part 903 is a 16-bit data space and includes segments each consisting of 4-bits: a first-stage hub address portion 903a, a second-stage hub address portion 903b, a third-stage hub address portion 903c, and a node address portion 903d. As described above, in the measuring apparatus 1, a plurality (three in this embodiment) of stages of hubs 93a, 93b, 93c, 93d, 93e, ... may be provided between the controller 9 and the functional blocks 200, 300, 400, 500, .... The first stage hub address portion 903a stores an address of a hub directly connected to the controller 9, the second stage hub address portion 903b stores an address of one of the hubs at the second stage from the controller 9, the third stage hub address portion 903c stores an address of one of the hubs at the third stage from the controller 9, i.e., an address of one of the hubs directly connected to the functional blocks 200, 300, 400, 500, . . . . The node address portion 903*d* stores an address assigned to a slave communication interface to which the packet is transmitted. Since each of the address portions 903*a*-903*d* is a 4-bit data space, up to 16 first-stage hubs may be designated, and up to 16 downstream (slave side) hubs connecting from each upstream (master side) hub may be designated. Also up to 16 functional blocks connecting from each third-stage hub may be designated.

As shown in FIG. 12, when the data in the address part 903 is "05AF" in hexadecimal notation, the address of the first stage hub is "0", the address of the second stage hub is "5", the address of the third stage hub is "A", and the address of the functional block is "F". This packet 900 is generated by the master communication interface 91*d* of the controller 9, and the master communication interface 91*d* transmits the packet 900 to the hub 93*a* having an address corresponding to the data "0" of the first stage address portion 903*a* included in the packet 900. Since the packet 900 is transmitted to a functional block from the controller 9, the aforementioned M/S bit 902*a* stores "1". Upon reception of the packet 900, the first stage hub 93*a* verifies that "1" is stored by referring the M/S bit 902*a*, and extracts data of the address part 903 from the packet 900. The hub 93*a* designated as the first stage hub determines that the stage to which the packet is to be transmitted next is the second stage based on the setting value of the setting part 109, and transmits the packet 900 to a hub 93*b* having an address corresponding to the data "5" of the second stage hub address portion 903*b*. The second stage hub 93*b* receives the packet 900 and determines that "1" is stored by referring the M/S bit 902*a* in the same manner as described above, extracts data in the address part 903, and transmits the packet 900 to the hub 93*e* having an address corresponding to the data "A" of the third stage hub address portion 903*c*. The third stage hub 93*e* determines that "1" is stored by referring to the M/S bit 902*a*, extracts the address part 903 from the packet 900, refers the data "F" of the node address portion 903*d* contained in the address part 903, and transmits the packet to the functional block 200 having this address. In this manner, the packet 900 is properly transmitted to the functional block 200 which is a destination of transmission.

The command part 904 is a segment for data that defines a content of processing after reception of a packet in the functional block. When there is no data in the command part 904, or when every bit is "0", the slave communication interface having received the packet transmits a reception confirming packet to the controller 9. The controller 9 receives the reception confirming packet to confirm that the packet has reached the functional block. The command part 904 may store a load command. A packet 900 containing a load command is usually transmitted to all of the functional blocks 200, 300, 400, 500, . . . at once by broadcasting communication. In other words, the BC bit 902*b* of the PRPTY part 902 of the packet 900 containing a load command is always "1". When the slave communication interface 210 (310, 410, . . . ) receives a packet in which a load command is stored in the command part 904, the slave communication interface 210 (310, 410, . . . ) reads out output data of each sensor in the transmitting buffer 221 (321, 421, . . . ), and stores in a memory provided in the slave communication interface 210 (310, 410, . . . ). The master communication interface 91*d* sequentially transmits a packet requesting transmission of sensor output data to each of the functional blocks 200, 300, 400, . . . , and upon reception of the transmission requesting packet, the slave communication interface 210 (310, 410, . . . ) generates a packet containing the output data stored in the memory, and transmits it to the controller 9. Upon reception of sensor output data from all of the functional blocks 200, 300, 400, . . . , the master communication interface 91*d* collectively gives all sensor output data to the CPU 91*a*. As a result, at the point of time when the packet containing a load command is transmitted to each of the functional blocks 200, 300, 400, . . . from the controller 9, sensor output data belonging to all of the functional blocks 200, 300, 400, . . . is acquired almost concurrently by the respective slave communication interfaces, and this output data is collected later by the controller 9. Therefore, the controller 9 acquires states of all mechanism units 2, 3, 4, . . . at the point of time when the load command is transmitted.

The command part 904 may store a latch command. The packet 900 containing the latch command is usually transmitted to all functional blocks 200, 300, 400, 500, . . . at once by broadcasting communication in the same manner as the case of the load command. In other words, the BC bit 902*b* of the PRPTY part 902 of the packet 900 containing the latch command is always "1". This latch command is a signal for instructing the driving circuits 220, 320, 420, . . . to start driving the mechanism units 2, 3, 4, . . . . The controller 9 transmits control data to each of the functional blocks 200, 300, 400, . . . before transmitting the latch command to each of the functional blocks 200, 300, 400, . . . . The control data is data representing contents of control of a mechanism unit (for example, rotation direction, rotation speed, rotation angle and the like of a stepping motor), i.e., data representing an operation command for the mechanism unit, and is generated by the CPU 91*a*. The CPU 91*a* generates plural sets of control data corresponding to each of the functional blocks 200, 300, 400, . . . , and give them to the master communication interface 91*d*. The master communication interface 91*d* generates a packet 900 containing an address of the slave communication interface of the functional block corresponding to the control data in the address part 903, and containing the control data in the data part 907 as will be described later, and transmits the packet to the functional block. The packet of the control data is sequentially transmitted to all of the functional blocks 200, 300, 400, . . . by the master communication interface 91*d*. Upon reception of the packet containing control data, the slave communication interfaces 210, 310, 410, . . . transmit a reception confirming packet in which data representing reception confirmation is stored to the controller 9, while writing the control data into the receiving buffers 222, 322, 422, . . . and turn into standby state. The communication interface 91*d* in standby state receives a reception confirming packet from each of the functional blocks 200, 300, 400, . . . after transmitting all packets of control data. Then after receiving the reception confirming packets from all of the functional blocks 200, 300, 400, . . . , the master communication interface 91*d* generates a packet containing a latch command, and transmits it to all of the functional blocks 200, 300, 400, . . . concurrently. All of the slave communication interfaces 210, 310, 410, . . . receive the latch command almost concurrently, and give an operation starting instruction to each driver included in the driving circuits 220, 320, 420, . . . , directly after reception of the latch command. Upon acceptance of an operation starting instruction, a driver reads out from the receiving buffers 222, 322, 422, . . . , control data transmitted from the controller 9 and drives a device in accordance with the control data. As a result, all of the functional blocks 200, 300, 400, . . . receive a latch command almost concurrently, and each driver starts driving a respective device, making it possible to operate the mechanism units 2, 3, 4, 5, . . . concurrently.

The data part 907 is a segment for data to be transmitted. When control data is transmitted from the controller 9 to the functional blocks 200, 300, 400, . . . , control data described above is stored in the data part 907 of the packet 900. When sensor output data is transmitted from the functional blocks 200, 300, 400, ... to the controller 9, the sensor output data is stored in the data part 907 of the packet 900.

By adopting the configuration as described above, when the master communication interface 91d transmits a packet containing a latch command, each mechanism unit 2, 3, 4, 5, ... operates concurrently, enabling concurrent control of the mechanism units 2, 3, 4, 5, .... In addition, since the functional blocks 200, 300, 400, 500, ... are so configured that the slave communication interfaces 210, 310, 410, 510, ... and the driving circuits 220, 320, 420, 520, ... are respectively provided for the mechanism units 2, 3, 4, 5, ..., the functional blocks 200, 300, 400, 500, ... and the controller 9 are independent from each other. Also it is not necessary to configure the controller 9 in conformance with the structures of the functional blocks 200, 300, 400, 500, ..., and hence the controller 9 accepts a variety of structures of functional block, and the controller 9 may be shared among plural types of devices. In the case where a requested specification differs among device types, a functional block that can be shared is shared with other types of devices, while the other functional blocks are constructed to satisfy the requested specification and the resultant functional block may be connected to the controller 9. This improves the developing efficiency of the measuring apparatus compared to conventional arts. For example, a reagent dispensing arm can be additionally provided in the aforementioned measuring apparatus 1, by connecting an additional reagent dispensing arm block having a structure similar to those of the reagent dispensing arm blocks 300, 400 to one of the hubs connected to the controller 9, and rewriting the control program. In other words, it is not necessary to change the design of the structural part of the controller 9 and the other measuring apparatus 51 in order to add such functional block, so that it is possible to reduce the number of processes for development compared to conventional arts.

In order to synchronously control the mechanism units 2, 3, 4, 5, ..., it is necessary to concurrently acquire the states of the mechanism units 2, 3, 4, 5, ..., i.e., output data of the respective sensors provided for the mechanism units. This is achieved by transmitting a load command by the controller 9.

Since a tree-like connection form is adopted in which a plurality of hubs serving as intermediate nodes are provided from the controller 9 and functional blocks 200, 300, 400, 500, ... are connected to ends of the respective hubs, it is not necessary to provide the controller 9 with a number of connection ports so that the controller 9 can be miniaturized. Further, it is not necessary to design the controller 9 in accordance with the configuration of the mechanism units, and hence the controller 9 may be shared among a plurality of devices.

In the present embodiment, explanation was made on the configuration where the controller 9 has only one connection port, and one hub 93a is connected to this controller 9, however, the present invention is not limited to this configuration, and the controller 9 may be provided with a plurality of connection ports to which hubs and functional blocks are connected. Alternatively, a plurality of functional blocks may be directly connected to the controller 9 without provision of a hub.

In the present embodiment, explanation was made on the case where a blood coagulation measuring apparatus is used as a measuring apparatus 1; however, other measuring apparatuses such as blood cell analyzers, immune analyzers, urinary formed element analyzers, urine qualitative analyzers, stool analyzer and particle analyzers may be used without limited thereto.

The foregoing detailed description and accompanying drawings have been provided by way of illustration, and are not intended to limit the scope of the appended claims. Many variations in the embodiments illustrated herein will be obvious to one of ordinary skill in the art, and remain within the scope of the appended claims and their equivalents.

What is claimed is:

1. A control method for operating a measuring apparatus having a plurality of mechanism units used for measurement of an analyte, the method comprising:
   by an operation instructor, issuing operation commands respectively for at least some of the mechanism units;
   by a master communicator provided for the operation instructor, transmitting the operation commands one at a time respectively to slave communicators respectively provided for the at least some mechanism units;
   by each of the slave communicators, receiving one of the operation commands transmitted from the master communicator;
   by a driver provided for a respective of the at least some mechanism units, temporarily storing one of the operation commands received by a corresponding slave communicator;
   by the master communicator, broadcasting an operation start instruction signal for initiation of an operation to the slave communicators;
   by the slave communicators, substantially concurrently receiving the operation start instruction signal broadcasted from the master communicator; and
   by the drivers, substantially concurrently executing the stored operation commands to drive the at least some mechanism units in concert, upon reception of the operation start instructing signal by the slave communicators.

2. A measuring apparatus conducting measurement of an analyte, the apparatus comprising:
   a plurality of mechanism units that include one or more of an analyte aspiration unit, a reagent aspiration unit, a fluid unit, and an optical measurement unit;
   an operation instructor that issues operation commands respectively for at least some of the mechanism units;
   a master communicator, provided for the operation instructor, that transmits the operation commands one at a time respectively to slave communicators respectively provided for the at least some mechanism units, wherein the slave communicators each receive one of the operation commands transmitted from the master communicator; and
   drivers, provided respectively for the at least some mechanism units, that each temporarily store one of the operation commands received by a corresponding slave communicator, wherein
   the master communicator broadcasts an operation start instruction signal for initiation of an operation to the slave communicators, after transmitting the operation commands to the slave communicators; and
   triggered by reception of the broadcasted operation start instruction signal by the slave communicators, the drivers substantially concurrently execute the stored operation commands to drive the at least some mechanism units in concert.

3. The measuring apparatus according to claim 2, wherein each driver has a memory for storing the operation command received by the corresponding slave communicator, and drives the corresponding mechanism unit in accordance with the operation command stored in the memory when the slave communicator receives the operation start instructing signal.

4. The measuring apparatus according to claim 2, wherein the master communicator and the slave communicators are connected in a tree form via communication wires.

5. The measuring apparatus according to claim 4, further comprising:
a relay device for relaying communication between the master communicator and the slave communicators, the relay device being provided between the master communicator and the slave communicators, and having a master-side connection port connected to the master communicator and a plurality of slave-side connection ports connected to the slave communicators.

6. The measuring apparatus according to claim 2, wherein communication between the master communicator and the slave communicators comprises serial communication.

7. The measuring apparatus according to claim 2, wherein communication between the master communicator and the slave communicators comprises packet communication.

8. The measuring apparatus according to claim 7, wherein a packet transmitted from the master communicator to the slave communicators includes communication information representing whether or not to broadcast the packet to the slave communicators.

9. The measuring apparatus according to claim 7, wherein the slave communicators transmit a reception confirming packet for confirming reception of the operation commands to the master communicator when the slave communicators receive the operation commands, and the master communicator transmits the operation start instruction signal when the master communicator receives a reception confirming packet from all of the slave communicators.

10. The measuring apparatus according to claim 2, wherein
the mechanism units each have a detector for detecting a state of a corresponding mechanism unit,
the measuring apparatus further comprises a transmission buffer provided in the respective mechanism units,
the operation instructor issues a state load command for loading the states of the at least some of the mechanism units detected by the detectors;
the master communicator broadcasts the state load command issued by the operation instructor to the slave communicators of the at least some mechanism units,
the transmission buffers of the at least some mechanism units store the detection results of the detectors when the corresponding slave communicators receive the broadcasted state load command; and
after receiving the broadcasted state load command, the slave communicators transmit the detection results stored in the transmission buffers to the operation instructor in response to reception of a transmission request command transmitted from the master communicator.

11. The measuring apparatus according to claim 2, wherein the analyte comprises a blood analyte.

12. The measuring apparatus according to claim 2, wherein the analyte comprises a urine analyte.

13. The measuring apparatus according to claim 2, wherein the analyte comprises a particulate analyte containing particles.

14. The measuring apparatus according to claim 2, wherein at least one of the plurality of mechanical units comprises at least one of an analyte dispensing arm block, a reagent dispensing arm block, a table block or a fluid block.

15. The measuring apparatus according to claim 4, wherein a relay device provides a communication link between the operation instructor and one of the plurality of mechanism units which is adaptive to removal and addition of a mechanism unit to and from the measuring apparatus.

16. A measuring apparatus comprising:
a plurality of mechanism units;
an operation instructor that issues operation commands respectively for at least some of the mechanism units;
a master communicator, provided for the operation instructor, that transmits the operation commands one at a time respectively to slave communicators respectively provided for the at least some mechanism units, wherein the slave communicators each receive one of the operation commands transmitted from the master communicator; and
drivers, provided respectively for the at least some mechanism units, that each temporarily store one of the operation commands received by a corresponding slave communicator, wherein
the master communicator broadcasts an operation start instruction signal for initiation of an operation to the slave communicators, after transmitting the operation commands to the slave communicators; and
triggered by reception of the broadcasted operation start instruction signal by the slave communicators, the drivers substantially concurrently execute the stored operation commands to drive the at least some mechanism units in concert,
wherein the plurality of mechanism units include:
an analyte aspiration unit that aspirates a blood analyte from a container containing the blood analyte;
a reagent aspiration unit that aspirates a reagent from a reagent container containing the reagent to be mixed with the blood analyte;
a fluid unit that mixes the blood analyte aspirated by the analyte aspiration unit and the reagent aspirated by the reagent aspiration unit; and
an optical measurement unit that measures a mixed sample mixed by the fluid unit for the measurement items by optical means.

17. A control system for a measuring apparatus conducting measurement of an analyte, the control system comprising:
a plurality of mechanism units each having a state detector the mechanism units including one or more of an analyte aspiration unit, a reagent aspiration unit, a fluid unit, and an optical measurement unit;
a controller that controls operation of the plurality of mechanism units;
a transmission buffer, provided in the respective mechanism units, that stores a detection result from a corresponding state detector indicating a state of a corresponding mechanism unit;
a command issuer that issues a state load command for loading states of the mechanism units detected by their state detectors; and
a master communicator that broadcasts the state load command to slave communicators respectively provided for at least some mechanism units, wherein the slave communicators substantially concurrently receive the state load command broadcasted from the master communicator and the transmission buffers of the at least some mechanism units load the detection results from the state detectors when the slave communicators receive the broadcasted state load command, and
after receiving the broadcasted state load command, the slave communicators transmit the detection results loaded in the transmission buffers to the controller in response to reception of a transmission request command transmitted from the master communicator.

18. The control system according to claim 17, wherein the master communicator and the plurality of slave communicators are connected in a tree configuration via communication wires.

19. The control system according to claim 18, further comprising:
a relay device for relaying communication between the master communicator and the slave communicators, the relay device being provided between the master communicator and the slave communicators, and having one master-side connection port connected to the master communicator and a plurality of slave-side connection ports connected to the slave communicators.

20. The control system according to claim 17, wherein communication between the master communicator and the slave communicators comprises serial communication.

21. The control system according to claim 17, wherein communication between the master communicator and the slave communicator comprises packet communication.

22. The control system according to claim 21, wherein a packet transmitted from the master communicator to the slave communicators includes communication information representing whether or not to broadcast the packet to the slave communicators.

23. An analyzer for analyzing a medical diagnostic sample, comprising:
functional blocks, each of the functional blocks comprising, a mechanism unit, a detection device and a drive device, wherein the drive device is configured to process the medical diagnostic sample for analysis, and the detection device is configured to make a detection in relation to the drive device, and the mechanism units include one or more of an analyte aspiration unit, a reagent aspiration unit, a fluid unit, and an optical measurement unit;
a controller configured to transmit a control command to each of the functional blocks to control the detection device and the drive device, and receive a detection result from each of the functional blocks; and
a communication hub configured to route the control command and the detection result between the controller and each of the functional blocks,
wherein the communication hub is connectible in series to another communication hub and comprises an upstream communication port and a downstream communication port, such that the at least one communication hub provides a communication link between the controller and the functional blocks, at least one of the functional blocks being adaptive to a removal and an addition of a functional block to and from the analyzer,
wherein the controller is configured to broadcast a synchronizing command to the functional blocks after transmitting the control commands to the functional blocks, and
wherein the functional blocks concurrently execute the control commands in response to the broadcasted synchronizing command.

24. A method for synchronizing operations in an analyzer for analyzing a medical diagnostic sample, wherein the analyzer comprises a controller and functional blocks, the method comprising:
receiving and storing a control command at each of the functional blocks sent from the controller via a communication hub, each of the functional blocks comprising a detection device and a drive device, wherein the drive device is configured to process the medical diagnostic sample for analysis, and the detection device is configured to make a detection in relation to the drive device;
subsequently to receiving the control command, receiving at each of the functional blocks a synchronizing command broadcasted from the controller via the communication hub; and
in response to reception of the broadcasted synchronizing command, concurrently executing the stored control command at each of the functional blocks to operate the functional blocks in concert.

* * * * *